United States Patent
Juncker et al.

(10) Patent No.: US 11,493,505 B2
(45) Date of Patent: Nov. 8, 2022

(54) COLOCALIZATION-BY-LINKAGE SANDWICH ASSAYS

(71) Applicant: Nomic Bio Inc., Montreal (CA)

(72) Inventors: David Juncker, Verdun (CA); Milad Dagher, Montreal (CA)

(73) Assignee: Nomic Bio Inc.

( * ) Notice: Subject to any disclaimer, the term of this patent is extended or adjusted under 35 U.S.C. 154(b) by 0 days.

(21) Appl. No.: 16/898,338

(22) Filed: Jun. 10, 2020

(65) Prior Publication Data

US 2020/0319173 A1 Oct. 8, 2020

Related U.S. Application Data

(63) Continuation of application No. PCT/CA2019/050405, filed on Apr. 3, 2019.

(60) Provisional application No. 62/651,943, filed on Apr. 3, 2018.

(51) Int. Cl.
*G01N 33/543* (2006.01)
*G01N 33/53* (2006.01)
*C12Q 1/6804* (2018.01)

(52) U.S. Cl.
CPC ..... *G01N 33/54306* (2013.01); *C12Q 1/6804* (2013.01); *G01N 33/5308* (2013.01); *C12Q 2537/143* (2013.01); *G01N 2400/00* (2013.01); *G01N 2458/00* (2013.01); *G01N 2458/10* (2013.01)

(58) Field of Classification Search
CPC .................................. C12Q 1/68; G01N 33/53
See application file for complete search history.

(56) References Cited

U.S. PATENT DOCUMENTS

| | | | |
|---|---|---|---|
| 5,695,926 A * | 12/1997 | Cros | C12Q 1/6813 435/5 |
| 7,306,904 B2 | 12/2007 | Landegren et al. | |
| 8,268,554 B2 | 9/2012 | Schallmeiner | |
| 9,481,945 B2 | 11/2016 | Juncker et al. | |
| 2016/0153973 A1 * | 6/2016 | Smith | G01N 33/54353 506/9 |

FOREIGN PATENT DOCUMENTS

| | | |
|---|---|---|
| EP | 0703296 A1 | 3/1996 |
| EP | 3102698 B1 | 1/2019 |
| WO | WO-2007044903 A2 | 4/2007 |
| WO | WO-2019191838 A1 | 10/2019 |

OTHER PUBLICATIONS

Li et al. A new class of homogenous nucleic acid probes based on specific displacement hybridization. Nucleic Acids Research; 2002; vol. 30: No. 2 e5: p. 1-9). (Year: 2002).*
Dagher et al., Ensemble multicolour FRET model enables barcoding at extreme FRET levels. Nature Nanotechnology 13: 925-932 (2018).
Fu et al., Multiplex Assays for Biomarker Research and Clinical Application: Translational Science Coming of Age. Proteomics Clin Appl. 4(3):271-284 (2010).
Jani et al., Multiplexed immunoassays by flow cytometry for diagnosis and surveillance of infectious diseases in resource-poor settings. The Lancet 2(4): 243-250 (2002).
Krishhan et al., Multiplexed Microbead Immunoassays by Flow Cytometry for Molecular Profiling: Basic Concepts and Proteomics Applications. Crit Rev Biotechnol. 29(1): 29-43 (2009).
Li et al., Novel Antibody Microarray Technologies for Multiplex Protein Analysis in Complex Samples. Doctor of Philosophy Department of Biomedical Engineering. McGill University, Montreal, Quebec, Canada 180 pages (2011).
Tighe, et al. ELISA in the multiplex era: Potentials and pitfalls. Proteomics—Clinical Applications. 9 (2015): 406-422.
Huiyan, Novel antibody microarray technologies for multiplex protein analysis in complex samples. Doctor of Philosophy Department of Biomedical Engineering, McGill University. Montreal, Quebec, Canada (2014). 180 pages.
PCT/CA2019/050405 International Search Report and Written Opinion dated Jun. 17, 2019.
Tighe et al., Utility, Reliability and Reproducibility of Immunoassay Multiplex Kits. Methods 61(1):23-29 (2013).
Indian Patent Application No. 202017043052 Office Action dated Apr. 22, 2022.

* cited by examiner

*Primary Examiner* — Ethan C Whisenant
(74) *Attorney, Agent, or Firm* — Wilson Sonsini Goodrich & Rosati

(57) ABSTRACT

There are provided methods and systems for detecting and/or quantifying an analyte. In particular, there are provided methods and systems for simultaneous detection and/or quantitation of two or more analytes in a sample. In some embodiments, there are provided colocalization-by-linkage assays on microparticles (CLAMP) comprising two sets of binders pre-assembled on a support, such that the two sets of binders are colocalized before contacting the sample.

18 Claims, 13 Drawing Sheets
(13 of 13 Drawing Sheet(s) Filed in Color)

Singleplex Sandwich Assay

Multiplex Sandwich Assay

Colocalization-by-Linkage Assay

COLOCALIZATION-BY-LINKAGE SANDWICH ASSAYS

CROSS-REFERENCE

This application is a continuation of International Application No. PCT/CA2019/050405, filed on Apr. 3, 2019, which claims the benefit of U.S. Provisional Patent Application No. 62/651,943, filed on Apr. 3, 2018.

FIELD

This invention relates to the field of bio-analysis and more particularly to systems and methods for detecting and/or quantifying a biomolecule using a colocalization-by-linkage sandwich assay, and to multiplexed sandwich assays for simultaneous detection and/or quantitation of multiple biomolecules in a sample.

BACKGROUND

Rapid and specific detection of biological cells and biomolecules, such as red blood cells, white blood cells, platelets, proteins, DNA, and RNA, has become increasingly important in diverse fields such as genomics, proteomics, diagnoses, therapeutics, and pathological studies. For example, the rapid and accurate detection of specific antigens and viruses is critical for combating pandemic diseases such as AIDS, flu, and other infectious diseases. The maturation of genomic technologies and advances in personalized medicine will require faster and more sensitive assays for detecting and quantifying large numbers of cells and biomolecules. Advances in medical research will increasingly rely on the accurate, timely, and cost-effective assessment of multiple proteins through proteomics. However, current automated, highly-sensitive and low-cost assays cannot be multiplexed efficiently.

The sandwich assay is one of the most popular formats for biological assays. In this format, a capture probe molecule is immobilized on a surface. A biological sample containing a target cell or biomolecule of interest is then applied to the surface. The target binds in a concentration dependent manner to the capture probe molecule immobilized on the surface. In a subsequent step, a detection probe molecule is applied to the surface. The detection probe molecule binds to the target biomolecule which is thus "sandwiched" between the capture probe and the detection probe molecules. In some assays, a secondary probe which can bind the detection probe molecule is also applied to the surface. The secondary probe can be conjugated to a label such as a fluorophore, in which case the binding can be detected using a fluorescence scanner or a fluorescence microscope. In some cases, the secondary probe is conjugated to a radioactive element, in which case the radioactivity is detected to read out the assay result. In some cases, the secondary probe is conjugated to an enzyme, in which case a solution containing a substrate is added to the surface and the conversion of the substrate by the enzyme is detected. In all cases the intensity of the signal detected is proportional to the concentration of the target in the biological sample. The requirement of dual recognition in a sandwich assay provides a highly-fidelity signal with low background noise and, as a result, high sensitivity detection.

The enzyme-linked immunosorbent assay (ELISA) is a well-known example of a sandwich assay. The ELISA typically uses antibodies and a color change reaction to identify a biomolecule in a biological sample. For example, an ELISA can use a solid-phase enzyme immunoassay (EIA) to detect the presence of a biomolecule, such as an antigen, in a liquid or wet biological sample applied to the solid-phase. ELISAs are often performed in 96-well or 384-well polystyrene plates, which passively bind antibodies and proteins. It is this binding and immobilization of reagents on a solid surface that makes ELISAs so easy to design and perform. Immobilizing the reagents on the microplate surface makes it easy to separate the bound target biomolecules from unbound materials during the assay and to wash away non-specifically bound materials. In addition, the requirement for dual recognition by both capture and detection probe molecules provides high specificity. The ELISA is thus a powerful tool for measuring specific target biomolecules within a crude preparation.

Sandwich assays can be designed and fabricated to measure or detect multiple analytes in parallel (also called multiplexing). Mutiplexed sandwich assays (MSAs) can be carried out using microarrays, such as DNA microarrays, protein microarrays or antibody microarrays. A microarray is a collection of microscopic spots containing biomolecules attached to a substrate surface, such as a glass, plastic or silicon, which thereby form a "microscopic" array. Such microarrays can be used for example to measure the expression levels of large numbers of genes or proteins simultaneously. The biomolecules, such as DNAs, proteins or antibodies, on a microarray chip are typically detected through optical readout of fluorescent labels attached to a target molecule that is specifically attached or hybridized to a probe molecule. The labels used may consist for example of an enzyme, radioisotopes, or a fluorophore.

MSAs can also be conducted on particles. In this case, particles suspended in solution are attached to biomolecules necessary to capture the targets of interest, such as proteins or specific DNA molecules. To conduct assays in multiplex, the particles must be encoded to allow the different assays in solution to be distinguished. A popular format is spectrally-encoded microparticles, which are encoded using fluorescent or luminescent dyes. Particles can also be encoded graphically—hence they are often referred to as "barcoded particles". Particle sizes may range in size from nanometer (nanoparticles) to micrometer (microparticles). Of these, fluorescently-encoded microparticles can be read-out rapidly and with high-throughput on cytometers.

However, current sandwich assays have poor performance when used to measure multiple biomolecules in a sample at the same time (multiplexing). Multiplexed ELISAs are limited by cross-reactivity between reagents such as antibodies, proteins, etc., and are prone to nonspecific signaling as a result. In conventional multiplexed sandwich assays in both array and bead formats, detection antibodies are typically applied as a mixture, but this method gives rise to interactions among reagents that constitute a liability for cross-reactivity. The application of detection antibody mixtures hence leads to spurious binding and generates false-positive signals from non-specific binding events, for example, between a capture and a non-targeted analyte (illustrated in FIG. 1 herein) that can be difficult to distinguish from the real target protein-binding signal. Such reagent-driven cross-reactivity is an inherent problem in MSAs and scales quadratically with the number of targets, severely limiting the scale of multiplexing. Due to problems with cross-reactivity, current MSAs are generally limited to 30-40 targets. Even then, lengthy and costly optimization protocols are needed to uncover and remove cross-reactive reagents (e.g., antibodies), which severely limits the applicability of these assays and increases their cost.

Cross-reactivity also hinders other types of multiplexed assays. For example, accurate protein phosphorylation analysis can be used to reveal cellular signaling events not evident from protein expression levels. Current methods and workflows for quantifying the fraction of post-translational modification (PTM) of a specific protein are severely limited in multiplexing because PTM-specific antibodies often possess inadequate specificity for the protein itself (that is, a phosphor-specific antibody is highly susceptible to the problem of reagent-driven cross-reactivity). As a result, conventional PTM panels are not multiplexed.

Conventional sandwich immunoassays are also not suitable for analyzing protein-protein interactions. Protein-protein interactions are a key part of cellular processes and understanding modulators of these interactions is extremely important to address correlating diseases. However, the use of detection antibody mixtures allows unwanted interactions and leads to spurious binding that can obfuscate the interaction signals. Current multiplexed sandwich assays are also costly because expensive reagents such as antibodies are used inefficiently during manufacturing and performance of the assays. For example, the addition of antibody mixtures in solution necessitates high concentrations (nanomolar), whereas the amount needed to bind to proteins to quantitate for microarrays or microbeads is 3 orders of magnitude less, which corresponds to a 99.9% loss of antibodies. Further, the sensitivity of a given sandwich immunoassay is highly affected by background signal which is often due to non-specific binding and/or incomplete washing of labeled detection antibodies. Methods to reduce incomplete washing by increasing washing cycles and including additive reagents have been used, however these methods result in increased assay times and assay complexity.

U.S. Pat. No. 9,481,945 describes antibody colocalization microarrays (ACM) which depends on the addressing of each capture antibody spot on a microarray by a single detection antibody, thus avoiding interaction between antibody reagents and reproducing assay conditions that are found in single-plex ELISA assays. Execution of this method requires first spotting the capture antibody, removing the slide from the spotter, incubating it with sample, washing and rinsing it as needed, and placing it back for the spotting of the detection antibody followed by binding and incubation. This method thus depends on the transfer of n different reagents to n spots each with a different reagent as well, representing an n-to-n transfer. The need to perform spotting as part of the assay is cumbersome and slow and throughput is limited.

U.S. Pat. No. 7,306,904 describes assays for detection and/or quantification of one or several analyte(s) is solution using so called proximity probes. The proximity probes comprise a binding moiety and a nucleic acid. The nucleic acid from one proximity probe is only capable of interaction with the nucleic acid from the other proximity probe when these are in close proximity, i.e. have bound to the analytes for which they are specific. However, in general multiplexed proximity-based assays require detection or read-out in single-plex format and hence necessitate complex microfluidics to fractionate the sample into n fractions for n-plex assays.

U.S. Patent Application Publication No. US 2016/0153973 describes a method and system which uses cleavable linkers to detect an analyte in an immunoassay. However, the method and system is not suitable for multiplexing or simultaneous detection of multiple analytes in an immunoassay with high sensitivity, due to high background signal and cross-reactivity between reagents.

SUMMARY

There are provided methods and systems for detection and/or quantification of biomolecules using biochemical assays. It is an object of the invention to ameliorate at least some of the deficiencies present in the prior art. Embodiments of the present technology have been developed based on the inventors' appreciation that there is a need for scalable, cost-efficient, sensitive, rapid and/or simple multiplexing sandwich assays, for example to replace the ELISA for routine use. In some aspects therefore, there are provided herein multiplex sandwich assays, including multiplex sandwich immunoassays with minimal cross-reactivity between reagents that are rapid, sensitive, cost-effective and/or scalable, allowing simultaneous detection and/or quantification of multiple analytes in a sample.

Methods and systems provided herein are based, at least in part, on the design and construction of linkages between reagents and supports, wherein the linkages enable addressable and programmable topology and function. Without wishing to be limited by theory, it is believed the systems and methods provided herein can reduce or eliminate one or more sources of background noise and/or false-positives in multiplexed sandwich assays. In some embodiments, cross-reactivity between reagents in multiplexed assays is minimized or eliminated by minimizing or eliminating interactions between non-cognate affinity binders. In some embodiments, methods and systems provided herein can reduce or eliminate background noise caused by incomplete washing and/or non-specific binding of detection reagents. In some embodiments, methods and systems provided herein can allow multiplexed detection of post-translational modifications and/or identification of protein-protein interactions through assembly of combinatorial reagent pairs on distinct assay supports. In some embodiments, surface architecture, linker lengths, and/or surface spacing of reagents can be controlled to modulate stringency of binding and signal generation. In some embodiments, additional steps allow stabilizing an assay signal by transducing it from a reversible reaction into stable oligo hybrids to minimize unbinding and hence minimize signal loss after assay completion and thereby increase sensitivity.

In a first aspect, there is provided a biomolecule complex for the detection and/or quantitation of an analyte in a sample, comprising:
an anchor strand attached to a support;
a capture reagent attached to the support; and
a detection reagent releasably attached to the anchor strand, the detection reagent or the anchor strand being optionally attached to a first label, the first label being inactive or undetectable;
wherein: the capture reagent and the detection reagent can simultaneously bind to the analyte, if present in the sample, forming a tertiary complex; release of the detection reagent from the anchor strand can release the detection reagent from the support in the absence of the analyte; and the first label can be activated or detected when the detection reagent is released from the anchor strand. The presence of the analyte in the sample is thus determined through detection of the first label on the support after the detection reagent has been released from the anchor strand, since the detection reagent will only remain attached to the support if bound to the analyte in a tertiary complex with the capture reagent. In some embodiments, therefore, the first label is only detected on the support when the analyte is present.

In some embodiments, the amount of the first label on the support, or detected on the support, when the detection reagent is released from the anchor strand is proportional to the quantity and/or concentration of the analyte in the sample.

In some embodiments, the detection reagent or the anchor strand is optionally attached to the first label. In some embodiments, the detection reagent is optionally attached to the first label. In some embodiments, the anchor strand is optionally attached to the first label.

In some embodiments, the detection reagent is releasably attached to the anchor strand directly via a covalent bond, a biotin-streptavidin bond, hydrogen bonding, a hydrophobic interaction, affinity binding, or a non-covalent interaction.

In other embodiments, the detection reagent is attached to the anchor strand indirectly via a hook strand, the detection reagent being linked to the hook strand and the hook strand being releasably attached to the anchor strand, wherein release of the hook strand from the anchor strand can release the detection reagent from the support in the absence of the analyte, and the first label can be activated or detected when the hook strand is released from the anchor strand. In some such embodiments, the amount of the first label on the support when the hook strand is released from the anchor strand is proportional to the quantity and/or concentration of the analyte in the sample.

In some embodiments, at least one of the detection reagent and the hook strand is optionally attached to the first label. For example, the first label may be attached to the hook strand; the first label may be attached to the detection reagent; or the first label may be attached to both the hook strand and the detection reagent. In some embodiments, the first label is absent, i.e., not attached to either the first strand or the detection reagent, e.g., where a second label is attached to a different component in the biomolecule complex.

In some embodiments, the capture reagent is attached to the support directly, e.g., via a covalent bond, a biotin-streptavidin bond, an oligonucleotide linker (such as a DNA oligonucleotide linker), or a polymer linker (such as a polyethylene glycol (PEG) linker). In other embodiments, the capture reagent is attached to the support indirectly, e.g., via linkage to the anchor strand attached to the support, e.g., via an oligonucleotide linker, a polymer linker, or a covalent bond. It should be understood that the capture reagent may be attached to the support using any suitable means, including chemical interaction, affinity binding, etc.

In some embodiments, the anchor strand is a polymer such as PEG or an oligonucleotide such as a single-stranded DNA oligonucleotide, a single-stranded RNA oligonucleotide, or a double-stranded DNA or RNA oligonucleotide. It should be understood that the anchor strand may be attached to the support using any suitable means, such as covalent bond, chemical interaction, affinity binding, a covalent bond, a biotin-streptavidin bond, a DNA oligonucleotide linker, a polymer linker, and the like.

The support is not particularly limited, and any suitable support may be used. Non-limiting examples of supports include microparticles (such as beads), the surface of a multi-well plate, the surface of a glass slide, or a hydrogel matrix. In some embodiments, the support is a bead or microparticle, typically micron-sized, such as without limitation a polystyrene bead, a magnetic bead, a paramagnetic bead, a plastic bead, and the like. In another embodiment, the support is a planar microarray. In some embodiments, the support is a barcoded bead, e.g., a bead attached to a fluorescent or luminescent dye or mixtures thereof, or a bead encoded spectrally, graphically, or chemically.

The hook strand attached to the detection reagent is generally a linker of sufficient length and flexibility to allow the detection reagent and the capture reagent to bind simultaneously to the analyte to form a tertiary complex. Non-limiting examples of hook strands include polymers such as PEG and oligonucleotides such as a single-stranded DNA oligonucleotide, a single-stranded RNA oligonucleotide, or a double-stranded DNA or RNA oligonucleotide.

In certain embodiments of the biomolecule complex provided herein, the hook strand is absent, and the detection reagent is releasably attached to the anchor strand directly, e.g., via a covalent bond, a biotin-streptavidin bond, affinity binding, or the like.

The capture reagent can be any molecule capable of specifically recognizing and binding to a target analyte. Non-limiting examples of capture reagents include antibodies, antigens, proteins, polypeptides, multi-protein complexes, exosomes, oligonucleotides, aptamers, modified aptamers (such as slow off-rate modified aptamers or somamers), and low molecular weight compounds. In certain embodiments, the capture reagent is an antibody and the analyte is an antigen, a protein, a polypeptide, a multi-protein complex, a hormone, or an exosome. In other embodiments, the capture reagent is an antigen, a protein, a polypeptide, a multi-protein complex, or an exosome, and the analyte is an antibody.

Similarly, the detection reagent can be any molecule capable of specifically recognizing and binding to a target analyte. Non-limiting examples of detection reagents include antibodies, antigens, proteins, polypeptides, multi-protein complexes, exosomes, oligonucleotides, and low molecular weight compounds. In certain embodiments, the detection reagent is an antibody and the analyte is an antigen, a protein, a polypeptide, a multi-protein complex, or an exosome. In other embodiments, the detection reagent is an antigen, a protein, a polypeptide, a multi-protein complex, or an exosome, and the analyte is an antibody.

It should be understood that if the capture reagent is an antibody and the analyte is an antigen, a protein, a polypeptide, a multi-protein complex, or an exosome, then the detection reagent is also an antibody capable of binding the analyte at the same time as the capture reagent. Similarly, if the capture reagent is an antigen, a protein, a polypeptide, a multi-protein complex, or an exosome and the analyte is an antibody, then the detection reagent will also be an antigen, a protein, a polypeptide, a multi-protein complex, or an exosome capable of binding the analyte at the same time as the capture reagent.

The capture reagent and the detection reagent may be the same or different, as long as they can both bind the target analyte at the same time, forming a tertiary complex. In some embodiments, the capture reagent and the detection reagent are both antibodies. They may be the same antibodies or different antibodies. They may be different antibodies that bind to the same epitope on the analyte, or they may be different antibodies that bind to different epitopes on the analyte. In the case where the capture reagent and the detection reagent bind the same epitope, they generally bind to different repeats of the epitope on the analyte, the analyte having two or more repeats of the epitope.

The analyte is not meant to be particularly limited and may be any biomolecule or biological cell for which detection and/or quantitation in a sample is desired. Non-limiting examples of analytes include an antigen, an antibody, a protein, a polypeptide, a multi-protein complex, a hormone, an exosome, an oligonucleotide, or a low molecular weight compound. Analytes may be detected in any sample of interest, particularly but not limited to biological samples, such as without limitation bodily fluids (e.g., urine, saliva, blood, serum, plasma, sweat), extracts (e.g., cellular extracts), and solutions containing proteins and/or DNA (e.g., reaction mixtures).

In some embodiments, the detection reagent is attached to the first label. In some embodiments, the hook strand is attached to the first label. In some embodiments, both the detection reagent and the hook strand are attached to the first label. In some embodiments where the first label is absent, neither the detection reagent nor the hook strand are attached to the first label.

In some embodiments, the releasable link between the hook strand and the anchor strand comprises a double-stranded DNA hybrid, the hook strand and the anchor strand comprising complementary single-stranded DNA oligonucleotides that hybridize together to form the double-stranded DNA hybrid. In some such embodiments, release of the hook strand from the anchor strand can be performed by raising the temperature so that the DNA hybrid "melts" or is unbound. For example, in embodiments where the melting temperature (Tm) of the double-stranded DNA hybrid is from about 50 to about 80 degrees Celsius, the temperature may be raised above the Tm such that the double-stranded DNA hybrid dissociates, thereby releasing the hook strand from the anchor strand.

In some embodiments, the biomolecule complex provided herein further comprises a displacer agent capable of releasing the hook strand from the anchor strand, thereby releasing the detection agent from the support in the absence of the analyte. The displacer agent may be any agent capable of specifically breaking or releasing the link between the hook strand and the anchor strand. For example, the displacer agent may be an enzyme or other agent that cleaves (or otherwise breaks) the releasable link between the hook strand and the anchor strand. Non-limiting examples of displacer agents include enzymes, light, and reducing agents such as DTT. The displacer agent may be capable, for example, of breaking the link between the hook strand and the anchor strand via an enzymatic reaction or by photocleavage.

In some embodiments, the displacer agent is an oligonucleotide. For example, when the releasable link between the hook strand and the anchor strand comprises a double-stranded DNA hybrid, the displacer agent can be a single-stranded DNA or RNA oligonucleotide that hybridizes to the hook strand or the anchor strand, thereby releasing the hook strand from the anchor strand via an oligonucleotide or DNA displacement reaction. In embodiments where the displacer agent hybridizes to the hook strand, the displacer agent forms a double-stranded DNA or RNA hybrid with the hook strand. In some such embodiments, the displacer agent can be detectably labeled, such that the displacer agent will only be retained on the support after washing if the detection reagent to which the hook strand is attached is bound to the analyte, detection of the label on the displacer agent thereby indicating presence of the analyte in the sample. In some such embodiments, the first label is absent, and detection of the label on the displacer agent is used to detect and/or quantitate the analyte. In some such embodiments, the amount of the label on the displacer agent detected on the support is proportional to the quantity and/or concentration of the analyte in the sample. In embodiments where the displacer agent hybridizes to the anchor strand, the displacer agent forms a double-stranded DNA or RNA hybrid with the anchor strand. It will be understood that in such embodiments, the displacer agent is not labeled, the label being attached instead to the detection reagent and/or the hook strand, such that label will only be detected on the support in the presence of the analyte.

In some embodiments, where the first label is absent, and detection of the label on the displacer agent is used to detect and/or quantitate the analyte, and the displacer agent acts via a DNA displacement reaction, the displacer agent binds (e.g., hybridizes) to the hook strand. In other embodiments, where the first label is present on the detection reagent or the hook strand and the displacer agent is not labeled, and the displacer agent acts via a DNA displacement reaction, the displacer agent may bind to either the hook strand or the anchor strand.

In some embodiments, the biomolecule complex further comprises a stem strand complementary to the surface-proximate sequence of the anchor strand, where the stem strand and the anchor strand are both single-stranded oligonucleotides, and the stem strand is capable of binding to the anchor strand to form a double-stranded oligonucleotide. In some embodiments, by forming a double-stranded oligonucleotide with the anchor strand, the stem strand can provide structural support to the anchor strand, e.g., to prevent the complex from collapsing onto the surface of the support, to provide rigidity, to create a spacer between the surface of the support and the complex, or to provide structural stability. In some embodiments, the stem strand can also be attached to a barcode, e.g., a fluorescent or luminescent dye, and used to attach a barcode label to the support. In general, the stem strand is attached to the anchor strand, e.g., by hybridization, and not covalently bound directly to the support.

In some embodiments where the biomolecule complex comprises a stem strand bound to the anchor to form a DNA hybrid proximate to the surface of the support, the anchor strand is attached to a label (instead of the detection reagent, the hook strand, or the displacer agent, which are all unlabeled). In these embodiments, the anchor strand is attached to a label that is inactive or undetectable when the anchor strand is hybridized to the stem strand; the anchor strand is also linked directly to the detection reagent. Upon cleavage of the DNA hybrid at a site between the label and the support, the label is activated or becomes detectable. The detection reagent will be released from the support in the absence of the analyte, so that signal is only detected in the presence of analyte and after cleavage (i.e., after release of the detection reagent).

In some embodiments, the relative density of the anchor strand and the capture reagent on the support can be adjusted to control the effective affinity of the assay. In some embodiments, the length of the hook strand can be adjusted to control the effective affinity of the assay.

In some embodiments, the valency of the conjugation between the detection reagent and the hook strand is selected to minimize cross-reactivity, to optimize performance in a multiplexed assay. In one embodiment, the conjugation between the detection reagent and the hook strand is monovalent. In other embodiments, the conjugation between the detection reagent and the hook strand is 1:2, 1:3, 1:4, 1:5, 1:6, 1:7 or 1:8, or less than 1:6, less than 1:8, or less than 1:10. In other embodiments, at least 90% of the detection reagent is linked to the support via only one hook strand.

In some embodiments where the capture reagent is linked to the anchor strand, the conjugation between the capture reagent and the linker to the anchor strand is monovalent. In some embodiments where the capture reagent is linked to the anchor strand, the conjugation between the capture reagent and the linker to the anchor strand is 1:2, 1:3, 1:4, 1:5, 1:6, 1:7 or 1:8, or less than 1:6, less than 1:8, or less than 1:10. In some embodiments, at least 90% of the capture reagent is linked to the anchor strand via only one capture strand.

In some embodiments, the anchor strand and/or the capture reagent are stochastically distributed on the support.

In some embodiments, the length and/or the flexibility of the hook strand can be selected so as to allow or optimize binding of the detection reagent to the analyte in the presence of the capture reagent.

In some embodiments where the link between the hook strand and the anchor strand is a double-stranded DNA hybrid, the melting temperature (Tm) of the double-stranded DNA hybrid is from about 50 to about 80 degrees Celsius.

In some embodiments, the concentration of the detection reagent after displacement is less than about 10 picomolar, to avoid re-binding of detection reagents to off-target reagents or analytes after the displacement or release has occurred.

In further embodiments, the biomolecule complex comprises two detection reagents, allowing a stronger signal to be generated since two copies of the label are present when the analyte is bound. In these embodiments, the biomolecule complex further comprises a second anchor strand linked to the support; a second detection reagent linked to a second hook strand, wherein the second hook strand is linked to the second anchor strand, and wherein at least one of the second detection reagent and the second hook strand is optionally attached to a third label; wherein the capture reagent, the detection reagent and the second detection reagent can simultaneously bind to the analyte, if present in the sample, forming a quaternary complex. Release of the second hook strand from the second anchor strand can release the second detection reagent from the support in the absence of the analyte and can activate the third label.

In some embodiments, the second detection reagent is attached to the third label. In some embodiments, the second hook strand is attached to the third label. The third label may be any suitable label, such as without limitation a fluorophore, a specific DNA sequence, or a biotin moiety.

In some embodiments where the third label is attached to the second detection reagent and/or the second hook strand and is inactive or undetectable, the third label can be activated or detected only when the second hook strand is released from the second anchor strand and the analyte is present.

In some embodiments, the biomolecule complex further comprises a second displacer agent capable of releasing the second hook strand from the second anchor strand, such that the second detection agent is released from the support in the absence of the analyte. The second displacer agent, like the displacer agent, can release the second hook strand from the second anchor strand by enzymatic reaction, by cleavage, or by oligonucleotide displacement reaction. The second displacer agent can also be detectably labeled, like the displacer agent, in which case the second detection reagent and the second hook strand are generally not labelled (i.e., the third label is absent). The second displacer agent may be the same or different from the displacer agent. In some embodiments, the second displacer agent and the displacer agent are the same, such that one agent can release both the second hook strand and the hook strand from their respective anchor strands.

In one embodiment, there is provided a biomolecule complex for the detection of an analyte in a sample, comprising an anchor strand linked to a support; a capture reagent, wherein the capture reagent is linked to the support; and a detection reagent linked to a hook strand, wherein the hook strand is linked to the anchor strand and wherein the detection reagent is also labeled; wherein the capture reagent and the detection reagent can simultaneously bind to the analyte, if present in the sample, forming a tertiary complex, and the link between the hook strand and the anchor strand can be broken, releasing the detection reagent from the support in the absence of the analyte.

In another embodiment, there is provided a biomolecule complex for the detection of an analyte in a sample, comprising an anchor strand linked to a support, a capture reagent, wherein the capture reagent is linked to a capture strand, wherein the capture strand is linked to the anchor strand; and a detection reagent linked to a hook strand, wherein the hook strand is linked to the anchor strand and wherein the detection reagent is also labeled; wherein the capture reagent and the detection reagent can simultaneously bind to the analyte, if present in the sample, forming a tertiary complex; the link between the hook strand and the anchor strand can be broken, releasing the detection reagent from the support in the absence of the analyte.

In a further embodiment, there is provided a biomolecule complex for the detection of an analyte in a sample, comprising an anchor strand linked to a support, a capture reagent linked to the support; a detection reagent, wherein the detection reagent is linked to a hook strand, wherein the hook strand is linked to the anchor strand; and a displacer agent capable of breaking the link between the anchor strand and the hook strand by binding to the hook strand, leading to the release of the detection reagent and hook strand from the support in the absence of the analyte, the displacer being labeled; wherein the capture reagent and the detection reagent can simultaneously bind to the analyte, if present in the sample, forming a tertiary complex.

In a further embodiment, there is provided a biomolecule complex for the detection of an analyte in a sample, comprising an anchor strand linked to a support, a capture reagent linked to a capture strand, wherein the capture strand is linked to the anchor strand; a detection reagent linked to a hook strand, wherein the hook strand is linked to the anchor strand; and a displacer agent capable of breaking the link between the anchor strand and the hook strand by binding to the hook strand, leading to the release of the detection reagent and the hook strand from the support in the absence of the analyte, the displacer agent being labeled; wherein the capture reagent and the detection reagent can simultaneously bind to the analyte, if present in the sample, forming a tertiary complex.

In another embodiment, there is provided a biomolecule complex for the detection of an analyte in a sample, comprising an anchor strand linked to a support, a capture reagent linked to the support; a detection reagent linked to a hook strand, wherein the hook strand is linked to the anchor strand and comprises an inactivated label; and a displacer agent capable of breaking the link between the anchor strand and the hook strand, leading to the release of the detection reagent and the hook strand from the support in the absence of the analyte; wherein the capture reagent and the detection reagent can simultaneously bind to the analyte, if present in the sample, forming a tertiary complex, and wherein breaking the link between the anchor strand and the hook strand activates the label on the hook strand.

In another embodiment, there is provided a biomolecule complex for the detection of an analyte in a sample, comprising an anchor strand linked to a support, a capture reagent linked to a capture strand, wherein the capture strand is linked to the anchor strand; a detection reagent linked to a hook strand, wherein the hook strand is linked to the anchor strand, the hook strand comprising an inactivated label; and a displacer agent capable of breaking the link between the anchor strand and the hook strand by binding to the anchor strand, leading to the release of the detection reagent and the hook strand from the support in the absence of the analyte; wherein the capture reagent and the detection reagent can simultaneously bind to the analyte, if present in the sample, forming a tertiary complex, and wherein breaking the link between the anchor strand and the hook strand activates the label on the hook strand.

In another embodiment, there is provided a biomolecule complex for the detection of an analyte in a sample, comprising an anchor strand linked to a support, a capture reagent linked to a capture strand, wherein the capture strand is linked to the anchor strand; a detection reagent linked to a hook strand, wherein the hook strand is linked to the anchor strand, the hook strand comprising an inactivated label; and a displacer agent capable of breaking the link between the anchor strand and the hook strand, leading to the release of the detection reagent and the hook strand from the support only in the absence of the analyte; wherein the capture reagent and the detection reagent are the same, and wherein the analyte has repeating epitopes, and the capture reagent and the detection reagent can simultaneously bind to the analyte, if present in the sample, forming a tertiary complex, wherein breaking the link between the anchor strand and the hook strand activates the label on the hook strand.

In a further embodiment, there is provided a biomolecule complex for the detection of an analyte in a sample, comprising an anchor strand linked to a support, a capture reagent linked to a capture strand, wherein the capture strand is linked to the anchor strand; a detection reagent linked to a hook strand, wherein the hook strand is linked to the anchor strand; and a displacer agent capable of breaking the link between the anchor strand and the hook strand by binding to the hook strand, leading to the release of the detection reagent and the hook strand from the support only in the absence of the analyte, wherein the displacer agent is labeled; wherein the capture reagent and the detection reagent are the same, and wherein the analyte has repeating epitopes, and the capture reagent and the detection reagent can simultaneously bind to the analyte, if present in the sample, forming a tertiary complex.

In another embodiment, there is provided a biomolecule complex for the detection of an analyte in a sample, comprising a first anchor strand linked to a support, a second anchor strand linked to the support, and a capture reagent linked to the support; a first detection reagent linked to a first hook strand, wherein the first hook strand is linked to the first anchor strand, the first hook strand comprising an inactivated first label; a second detection reagent linked to a second hook strand, wherein the second hook strand is linked to the second anchor strand, the second hook strand comprising an inactivated second label; a first displacer agent capable of breaking the link between the first anchor strand and the first hook strand, leading to the release of the first detection reagent and the first hook strand from the support in the absence of the analyte; and a second displacer agent capable of breaking the link between the second anchor strand and the second hook strand, leading to the release of the second detection reagent and the second hook strand from the support only in the absence of the analyte, wherein the capture reagent, the first detection reagent, and the second detection reagent can simultaneously bind to the analyte, if present in the sample, forming a quaternary complex, wherein breaking the link between the anchor strand and the first hook strand activates the first label on the first hook strand, wherein breaking the link between the anchor strand and the second hook strand activates the second label on the second hook strand.

In another embodiment, there is provided a biomolecule complex for the detection of an analyte in a sample, comprising a first anchor strand linked to a support, a second anchor strand linked to the support, and a capture reagent linked to the support; a first detection reagent linked to a first hook strand, wherein the first hook strand is linked to the first anchor strand; a second detection reagent linked to a second hook strand, wherein the second hook strand is linked to the second anchor strand; a first displacer agent capable of breaking the link between the first anchor strand and the first hook strand by binding to the first hook strand, leading to the release of the first detection reagent and the first hook strand from the support in the absence of the analyte, wherein the first displacer agent is labeled; and a second displacer agent capable of breaking the link between the second anchor strand and the second hook strand by binding to the second hook strand, leading to the release of the second detection reagent and the second hook strand from the support only in the absence of the analyte, wherein the first displacer agent is labeled; wherein the capture reagent, the first detection reagent, and the second detection reagent can simultaneously bind to the analyte, if present in the sample, forming a quaternary complex.

In some embodiments, the support is a microparticle, the surface of a well plate, the surface of a glass slide, or a hydrogel matrix.

In some embodiments, the capture reagent and the detection reagent are antibodies. In some embodiments, the analyte is an antigen. In some embodiments, the analyte is a multi-protein complex. In some embodiments, the analyte is an exosome.

In other embodiments, the capture reagent and the detection reagent are antigens, and the analyte is an antibody.

In some embodiments, the capture reagent is linked to the support via a covalent bond or via a biotin-streptavidin bond. In some embodiments, the capture reagent is linked to the support via a DNA oligonucleotide linker or via a polymer linker such as a PEG linker. In some embodiments, the detection reagents are linked to the support via a polymer linker such as a PEG linker or via a DNA oligonucleotide linker.

In one embodiment, the hook strand, the anchor strand, and displacer agent are DNA oligonucleotides.

In a further embodiment, the link between the hook strand and the anchor strand is a double-stranded DNA hybrid.

In an embodiment, the link between the anchor strand and the support is a covalent bond or a biotin-streptavidin bond. In another embodiment, the anchor strand is attached to the support via a chemical interaction. It should be understood that the anchor strand may be attached to the support using any suitable means, such as without limitation a covalent bond, a biotin-streptavidin bond, a DNA oligonucleotide linker, a polymer linker, or another chemical interaction such as hydrogen bonding, a hydrophobic interaction, affinity binding, or a non-covalent interaction.

In a further embodiment, the displacer agent breaks the link between the hook strand and the anchor strands via a DNA strand displacement reaction.

In another embodiment, the displacer agent breaks the link between the hook strand and the anchor strands via an enzymatic reaction.

In an embodiment, the label is a fluorophore. In an embodiment, the label is a specific DNA sequence. In an embodiment, the label is a biotin moiety.

In another embodiment, the detection reagent recognizes the same antigen but not the same epitope as the capture reagent.

In another embodiment, the detection reagent recognizes a different epitope bound on the same antigen as bound by the capture reagent.

In another embodiment, the detection reagent recognizes an identical epitope on the same antigen as bound by the capture reagent.

In another embodiment, the biomolecule complex described herein further comprises a stem strand complementary to the surface-proximate sequence of the anchor strand, the stem strand rendering the anchor oligonucleotide double-stranded.

In an embodiment, the relative density of the anchor strand and the capture reagent is adjusted to control the effective affinity of the assay.

In another embodiment, the length of the detection of the analyte (e.g., the length of the hook strand) is adjusted to control the effective affinity of the detection.

In another embodiment, the conjugation between detection reagent and hook strand is monovalent.

In an embodiment, the anchor strand is stochastically distributed. In another embodiment, the capture reagent is stochastically distributed.

There is also provided a method for detecting an analyte from a sample, comprising providing a support, a capture reagent, an anchor strand, a hook strand, and a detection reagent, wherein the capture reagent is linked to the support, the anchor strand is linked the support and to the hook strand, wherein the hook strand is linked to the detection reagent, wherein the detection reagent is labeled; incubating the sample with the support allowing binding of the capture reagent and the detection reagent to different epitopes on the analyte; breaking the bond between the hook strand and the anchor strand, separating the detection reagent and hook strand from the support in the absence of the analyte bound to the capture reagent and the detection reagent; and quantifying an amount of the bound analyte by analyzing the detection reagent label remaining on the support, wherein the detection reagent label concentration remaining on the support is in proportion to the concentration of the analyte bound.

There is further provided a method for detecting an analyte from a sample, comprising providing a support, an anchor strand, a capture strand, a capture reagent, a hook strand, and a detection reagent, wherein the anchor strand is linked to the support, to the capture strand and the hook strand, the capture strand is linked to the capture reagent, and wherein the hook strand is linked to the detection reagent; incubating the sample with the support allowing binding of the capture reagent and the detection reagent to different epitopes on the analyte; breaking the bond between the hook strand and the anchor strand by separating the detection reagent and the hook strand from the support in the absence of the analyte bound to the capture reagent and the detection reagent; and quantifying an amount of the bound analyte by analyzing the detection reagent label remaining on the support, wherein the detection reagent label concentration remaining on the support is in proportion to the concentration of the analyte bound.

There is further provided a method for detecting an analyte from a sample, comprising providing a support, a capture reagent, an anchor strand, a hook strand, and a detection reagent, wherein the capture reagent is linked to the support, wherein the anchor strand is linked the support and to the hook strand, wherein the hook strand is linked to the detection reagent; incubating the sample with the support allowing binding of the capture reagent and detection reagent to different epitopes on the analyte; incubating with a displacer agent to break the bond between the hook strand and the anchor strand by binding to the hook strand, separating the detection reagent and the hook strand from the support in the absence of the analyte bound to both the capture reagent and the detection reagent, wherein the displacer agent is labeled; quantifying an amount of the bound analyte by analyzing the displacer agent label remaining on the support, wherein the displacer agent label concentration remaining on the support is in proportion to the concentration of the analyte bound.

In another embodiment, there is provided a method for detecting an analyte from a sample, comprising providing a support, an anchor strand, a capture strand, a capture reagent, a hook strand, and a detection reagent, wherein the anchor strand is linked to the support and to the capture strand, wherein the capture strand is linked to the capture reagent, the anchor strand is linked to the hook strand, and wherein the hook strand is linked to the detection reagent; incubating the sample with the support allowing binding of the capture reagent and the detection reagent to different epitopes on the analyte; incubating with a displacer agent to break the bond between the hook strand and the anchor strand by binding to the hook strand, separating the detection reagent and the hook strand from the support in the absence of the analyte bound to both the capture reagent and the detection reagent, wherein the displacer agent is labeled; and quantifying an amount of the bound analyte by analyzing the displacer agent label remaining on the support, wherein the displacer agent label concentration remaining on the support is in proportion the concentration of the analyte bound.

There is further provided a method for detecting an analyte from a sample, comprising providing a support, a capture reagent, an anchor strand, a hook strand, and a detection reagent, wherein the capture reagent is linked to the support, wherein the anchor strand is linked the support and to the hook strand, wherein the hook strand is linked to the detection reagent, wherein the hook strand comprises an inactivated label; incubating the sample with the support allowing binding of the capture reagent and the detection reagent to different epitopes on the same analyte; incubating with a displacer agent to break the bond between the hook strand and the anchor strand, separating the detection reagent and hook strand from the support in the absence of the analyte bound to both the capture reagent and the detection reagent, wherein separating the hook strand from the anchor strand activates the label on the hook strand; and quantifying an amount of the bound analyte by analyzing the hook strand label remaining on the support, wherein the hook strand label concentration remaining on the support is in proportion to the concentration of the analyte bound.

There is further provided a method for detecting an analyte from a sample, comprising providing a support, an anchor strand, a capture strand, a capture reagent, a hook strand, and a detection reagent, wherein the anchor strand is linked to the support, the capture strand and the hook strand, wherein the capture strand is linked to the capture reagent, wherein the hook strand is linked to the detection reagent and comprises an inactivated label; incubating the sample with the support allowing binding of the capture reagent and the detection reagent to different epitopes on the analyte; incubating with a displacer agent to break the bond between the hook strand and the anchor strand by binding to the anchor strand, separating the detection reagent and the hook strand from the support only in the absence of the analyte bound to both the capture reagent and the detection reagent, wherein separating the hook strand from the anchor strand activates the label on the hook strand; and quantifying an amount of the bound analyte by analyzing the hook strand label remaining on the support, wherein the hook strand label concentration remaining on the support is in proportion to the concentration of the analyte bound.

There is also provided a method for detecting an analyte from a sample, comprising providing a support, an anchor strand, a capture strand, a hook strand, a capture reagent and a detection reagent, wherein the anchor strand is linked to the support, to the capture strand and to the hook strand, wherein the capture strand is linked to the capture reagent, wherein the hook strand is linked to the detection reagent, wherein the hook strand comprises an inactivated label, and wherein the capture reagent and the detection reagent are structurally similar; incubating the sample with the support allowing binding of the capture reagent and the detection reagent to different epitopes on the analyte, wherein the epitopes are structurally similar; incubating with a displacer agent to break the bond between the hook strand and the anchor strand, separating the detection reagent and the hook strand from the support in the absence of the analyte bound to both the capture reagent and the detection reagent, wherein separating the hook strand from the anchor strand activates a label on the hook strand; and quantifying an amount of the bound analyte by analyzing the hook strand label remaining on the support, wherein the hook strand label concentration remaining on the support is in proportion to the concentration of the analyte bound.

There is further provided a method for detecting an analyte from a sample, comprising providing a support, an anchor strand, a capture strand, a hook strand, a capture reagent and a detection reagent, wherein the anchor strand is linked to the support, to the capture strand and the hook strand, wherein the capture strand is linked to the capture reagent, wherein the hook strand is linked to the detection reagent, and wherein the capture reagent and the detection reagent are structurally similar; incubating the sample with the support allowing binding of the capture reagent and the detection reagent to different epitopes on the analyte, wherein the epitopes are structurally similar; incubating with a displacer agent to break the bond between the hook strand and the anchor strand by binding to the hook strand, separating the detection reagent and the hook strand from the support in the absence of the analyte bound to both the capture reagent and the detection reagent, wherein the displacer agent is labeled; and quantifying an amount of the bound analyte by analyzing the displacer strand label remaining on the support, wherein the displacer strand label concentration remaining on the support is in proportion the concentration of the analyte bound.

In an embodiment, the capture reagent and the detection reagent are peptides. In an embodiment, the capture reagent is linked to the support via a DNA oligonucleotide linker. In another embodiment, the detection reagent is linked to the support via a PEG linker.

In a further embodiment, the hook strand, anchor strand, and displacer agents are DNA oligonucleotides. In an embodiment, the link between hook strand and the anchor strand is a double-stranded DNA hybrid. In a further embodiment, the link between the anchor strand and the support is a covalent bond. In an embodiment, the link between the anchor strand and the support is a biotin-streptavidin bond.

In an embodiment, the displacer agent breaks the link between the hook strand and the anchor strands via a DNA strand displacement reaction. In an embodiment, the displacer agent breaks the link between the hook strand and the anchor strands via a enzymatic reaction.

In another embodiment, the label is a biotin moiety.

In a further embodiment, the anchor strand is linked to the microparticles via a chemical interaction.

In another embodiment, the detection reagent recognizes the same antigen but not the same epitope as the capture reagent. In a further embodiment, the detection reagent recognizes a different antigen bound to the same antigen as bound by the capture reagent. In an embodiment, the detection reagent recognizes an identical epitope on a different location of the same antigen as bound by the capture reagent.

In an embodiment, the biomolecule complex described herein further comprises a stem strand complementary to the surface-proximate sequence of the anchor strand, rendering the anchor oligonucleotide double-stranded.

In an embodiment, the relative density of the anchor strands and the capture reagent are adjusted to control the effective affinity of the assay.

In an embodiment, the length of the detection of the analyte (e.g., the hook strand) is adjusted to control the effective affinity of the detection.

In an embodiment, the conjugation between the detection reagent and the hook strand is monovalent.

In another embodiment, the anchor strand is stochastically distributed.

In a further embodiment, the capture reagent is stochastically distributed.

There is also provided a multitude of complex detection systems for the detection of multiple analytes in a sample, comprising a multitude of supports; a multitude of capture reagents, wherein each capture reagent is bound to its respective support; a multitude of detection reagents, wherein each detection reagent is bound to its respective support via a linker, wherein the detection reagents are labeled; wherein on each support, the capture reagent and detection reagents can simultaneously bind to the support-specific analyte, if present in the sample, forming a tertiary complex; the linker between the detection reagents and their respective supports can be broken, releasing the detection reagent from the support in the absence of the analyte.

There is further provided a multitude of complex detection systems for the detection of multiple analytes in a sample, comprising a multitude of supports; a multitude of capture reagents, wherein each capture reagent is bound to its respective support; a multitude of detection reagents, wherein each detection reagent is bound to its respective support via a support-specific hook strand, wherein each hook strand comprises a support-specific inactivated label; a displacer agent, wherein the displacer agent is capable of breaking the bond between the multitude of hook strands and the multitude of supports, separating the detection reagents from their respective supports; wherein on each support, the capture reagent and detection reagents can simultaneously bind to the support-specific analyte, if present in the sample, forming a tertiary complex; wherein breaking the bond between the support and the hook strands activates the support-specific labels on the hook strands.

There is also provided a multitude of complex detection systems for the detection of multiple analytes in a sample, comprising a multitude of supports; a multitude of capture reagents, wherein each capture reagent is bound to its respective support; a multitude of detection reagents, wherein each detection reagent is bound to its respective support via a support-specific hook strand; a displacer agent, wherein the displacer agent is capable of breaking the bond between the multitude of hook strands and the multitude of supports, wherein upon breaking the bond between the hook strand and the support the displacer agent binds to the hook strand, wherein the displacer agent is labeled; wherein on each support, the capture reagent and detection reagents can simultaneously bind to the support-specific analyte, if present in the sample, forming a tertiary complex.

In an embodiment, there is also provided a multitude of complex detection systems for the detection of multiple analytes in a sample, comprising a multitude of supports; a multitude of capture reagents, wherein each capture reagent is bound to its respective support; a multitude of detection reagents, wherein every detection reagent is linked to its respective support, wherein each detection reagent comprises an inactivated label, wherein the link between the detection reagents and their respective supports can be broken; wherein on each support, the capture reagent and detection reagents can simultaneously bind to the support-specific analyte, if present in the sample, forming a tertiary complex, whereupon breaking the link between the detection reagents and their respective supports, the detection reagent label is activated.

There is additionally provided a method for detecting an analyte from a sample, comprising providing a support, an anchor strand, a capture strand, a hook strand, a capture reagent and a detection reagent, wherein the anchor strand is linked to the support, wherein the anchor strand is also linked to the capture strand, wherein the capture strand is linked to the capture reagent, wherein the anchor strand is also linked to the hook strand, wherein the hook strand is linked to the detection reagent; incubating the sample with the support, under a condition to allow binding of the capture and detection reagents to different epitopes on the same analyte; incubating with a displacer agent to break the bond between the hook and anchor strands by binding to the hook strand, separating the detection reagent and hook strand from the support only in the absence of the analyte bound to both the capture and detection reagents, wherein the displacer agent is labeled; quantifying an amount of the bound analyte by analyzing the displacer strand label remaining on the support, wherein the displacer strand label concentration remaining on the support is in proportion to changes in the concentration of the analyte bound.

There is further provided a method for detecting an analyte from a sample, comprising providing a support, an anchor strand, a capture reagent, a hook strand, and a detection reagent, wherein the anchor strand is linked to the support, wherein the capture reagent is linked to the support, wherein the anchor strand, wherein the hook strand is linked to the support, wherein the hook strand is linked to the detection reagent; incubating the sample with the support, under a condition to allow binding of the capture and detection reagents to different epitopes on the same analyte; breaking the bond between the hook strand and the support, separating the detection reagent and hook strand from the support only in the absence of the analyte bound to both the capture and detection reagents; incubating with a bridge strand, wherein the bridge strand links the anchor strand to hook strand, wherein the bridge strand is labeled quantifying an amount of the bound analyte by analyzing the bridge strand label remaining on the support, wherein the bridge strand label concentration remaining on the support is in proportion to changes in the concentration of the analyte bound.

In some embodiments, the hook strand is labelled via inclusion of a label sequence, i.e., a unique DNA sequence that can be detected. In some such embodiments, the hook strand further comprises a re-bind sequence; after release of the hook strand from the anchor strand using a displacer agent oligonucleotide that binds to the anchor strand, a bridge strand is added, where the bridge strand can bind to both the re-bind sequence on the hook strand and the anchor strand, thereby reconnecting the hook strand indirectly to the anchor strand. In such embodiments, after the label attached to the hook strand is activated or made detectable by release from the anchor strand, the hook strand with the active/detectable label is re-attached to the support.

In one embodiment, there is provided a biomolecule complex for the detection and/or quantitation of an analyte in a sample, comprising: a) an anchor strand attached to a support; b) a capture reagent attached to the support; c) a detection reagent linked to a hook strand, the hook strand being releasably attached to the anchor strand, the hook strand and the anchor strand being linked together by a double-stranded DNA hybrid; and d) a displacer agent comprising a DNA oligonucleotide complementary to at least a portion of the hook strand and capable of hybridizing to the hook strand, thereby releasing the hook strand from the anchor strand via a DNA displacement reaction, the displacer agent being detectably labeled; wherein: the capture reagent and the detection reagent can simultaneously bind to the analyte, if present in the sample, forming a tertiary complex; and release of the hook strand from the anchor strand by the displacer agent can release the detection reagent from the support in the absence of the analyte. In an embodiment, the capture reagent and the detection reagent are antibodies, the analyte is an antigen or a protein, and the support is a barcoded microparticle.

In a second aspect, there is provided a multiplex sandwich assay system for the simultaneous detection and/or quantitation of two or more analytes in a sample, the system comprising two or more biomolecule complexes as described herein, wherein each biomolecule complex is for the detection and/or quantitation of a different analyte in the sample.

In some embodiments, the two or more biomolecule complexes are attached to the same support. For example, the support may be a planar surface, the surface of a multi-well plate, the surface of a glass slide, a hydrogel matrix, a microparticle, etc. In such embodiments, each biomolecule complex is positioned at a separate place on the support, allowing each labeled complex (and hence each analyte) to be identified by its position.

In some embodiments, the two or more biomolecule complexes are attached to different supports, e.g., different barcoded microparticles. For example, a first biomolecule complex may be attached to a first bead which is barcoded, e.g., spectrally, graphically, or chemically, e.g., attached to a first fluorescent or luminescent dye or mixture of dyes, and a second biomolecule complex may be attached to a second bead which is also barcoded, e.g., spectrally, graphically, or chemically, e.g., attached to a second fluorescent or luminescent dye or mixture of dyes. After the first and second complexes have been assembled on their respective beads, they can be mixed and contacted with the sample together, allowing for simultaneous detection of the two different analytes in the sample. The barcoding on the beads allows each labelled complex (and hence each analyte) to be identified.

In some embodiments, one or more of the two or more biomolecule complexes comprises a second anchor strand, a second detection reagent linked to a second hook strand, etc., such that a quaternary complex is formed between the capture reagent, the two detection reagents and the analyte.

In some embodiments, the two or more biomolecule complexes all lack the optional first label on the detection reagent or the hook strand, the label being provided only on the displacer agent. In some embodiments, the same labeled displacer agent is used to release the respective hook strand from the respective anchor strand for each biomolecule complex, each biomolecule complex (and its respective analyte) being identified by its position on the surface or by barcoding of the surface, particularly where the surface is a microparticle. In other embodiments, a different displacer agent with a different label may be used for each biomolecule complex.

In some embodiments, the two or more biomolecule complexes may each detect and/or quantitate the same analyte, wherein each of the biomolecule complexes has a different effective affinity for the analyte. For example, the effective affinity of the biomolecule complex for the analyte can be selected by adjusting the length of the hook strand and/or the anchor strand and/or adjusting the surface densities of the capture reagent and/or the detection reagent. In this way, an analyte may be assayed over a large range of concentrations.

wherein the length of the hook strand and/or the anchor strand can be adjusted to control the effective affinity of the assay; and/or wherein the surface densities of the capture reagent and/or the detection reagent can be adjusted to control the effective affinity of the assay It should be understood that the number of analytes that may be detected and/or quantitated at the same time in a multiplex sandwich assay system is not particularly limited. In some embodiments, a multiplex sandwich assay system may be used for the simultaneous detection and/or quantitation of five or more analytes, ten or more analytes, 15 or more analytes, 20 or more analytes, 30 or more analytes, 40 or more analytes, 50 or more analytes, 75 or more analytes, or 100 or more analytes in a sample, the system comprising a respective biomolecule complex specific for each respective analyte. The multiplex sandwich assay system is thus easily scalable for large-scale multiplexing.

In a third aspect, there is provided a method for detecting and/or quantitating an analyte in a sample, using a biomolecule complex as described herein.

In some embodiments, there are provided methods for simultaneous detection and/or quantitation of two or more analytes in a sample, using two or more biomolecule complexes as described herein, wherein each biomolecule complex is for the detection and/or quantitation of a different analyte in the sample. In some embodiments, there are provided methods for the simultaneous detection and/or quantitation of two or more analytes in a sample using a multiplex sandwich assay system as described herein, the system comprising two or more biomolecule complexes as described herein, wherein each biomolecule complex is for the detection and/or quantitation of a different analyte in the sample. It should be understood that methods provided herein may be used for the simultaneous detection and/or quantitation of a large number of analytes in a sample, the methods being scalable to allow large-scale multiplexing.

In an embodiment, there is provided a method for detecting and/or quantitating an analyte in a sample, the method comprising: a) providing a support, a capture reagent attached to the support, an anchor strand attached to the support, and a detection reagent optionally linked to a hook strand, wherein the detection reagent or the hook strand is releasably linked to the anchor strand, and wherein at least one of the detection reagent and the hook strand is optionally attached to a first label, the first label being inactive or undetectable; b) contacting the support with the sample under conditions that allow simultaneous binding of the capture reagent and the detection reagent to the analyte, to form a tertiary complex; and c) adding a displacer agent optionally attached to a second label, wherein the displacer agent releases the detection reagent or the hook strand from the anchor strand, such that the detection reagent optionally linked to the hook strand is released from the support in the absence of the analyte, and wherein the release of the detection strand or the hook strand from the anchor stand activates the first label or makes the first label detectable.

In some embodiments, the method further comprises the following step: d) determining the presence and/or the amount of the first label and/or the second label on the support, wherein the presence of the first and/or the second label on the support indicates the presence of the analyte in the sample, and the amount of the first and/or the second label is proportional to the quantity and/or concentration of the analyte in the sample.

In some embodiments, the method further comprises a step of washing the support to remove any unbound reagents or materials after step (c).

In some embodiments, the method further comprises a step of storing the support after step (c).

In some embodiments of the methods provided herein, the support further comprises a second anchor strand attached to the support, a second capture reagent attached to the support, and a second detection reagent optionally linked to a second hook strand, wherein the second detection reagent or the second hook strand is linked to the second anchor strand, and wherein at least one of the second detection reagent and the second hood strand is optionally attached to a third label, the third label being inactive or undetectable, wherein the second capture reagent and the second detection reagent can bind simultaneously to a second analyte in the sample, to form a second tertiary complex; wherein the displacer agent also releases the second detection reagent or the second hook strand from the second anchor strand, such that the second detection reagent optionally linked to the second hook strand is released from the support in the absence of the second analyte, and wherein the release of the second detection reagent or the second hook strand from the second anchor stand activates the third label or makes the third label detectable; wherein the presence and/or the amount of the third label on the support indicates the presence of the second analyte in the sample, and the amount of the third label on the support is proportional to the quantity and/or concentration of the second analyte in the sample; such that the first analyte and the second analyte can be simultaneously detected and/or quantitated in the sample.

In some embodiments, the second anchor strand and the second capture reagent are positioned at a first location and a second location respectively on the support. In other embodiments, the second anchor strand and the second capture reagent are attached to a second support. The support and/or the second support may be, for example, a microparticle such as a polystyrene bead. In an embodiment, the first support is a first barcoded bead (i.e., a first bead encoded with a first barcode, such as a first fluorescent or luminescent dye or a first mixture of dyes), and the second support is a second barcoded bead (i.e., a second bead encoded with a second barcode, such as a second fluorescent or luminescent dye or a second mixture of dyes), allowing identification of the respective beads when the respective barcodes are detected.

In some embodiments, the first support and the second support are mixed together before being contacted with the sample. For example, the first support and the second support may be contacted with the sample simultaneously. The sample may be a biological sample, such as without limitation a bodily fluid, an extract, a solution containing proteins and/or DNA, a cell extract, a cell lysate, or a tissue lysate. Non-limiting examples of bodily fluids include urine, saliva, blood, serum, plasma, cerebrospinal fluid, tears, semen, and sweat.

In some embodiments, the method uses a hook strand that is labelled via inclusion of a label sequence, i.e., a unique DNA sequence that can be detected. In some such embodiments, the hook strand further comprises a re-bind sequence; after release of the hook strand from the anchor strand using a displacer agent oligonucleotide that binds to the anchor strand, and optional washing, a bridge strand is added, wherein the bridge strand binds to both the re-bind sequence on the hook strand and the anchor strand, thereby reconnecting the hook strand indirectly to the anchor strand. In such embodiments, after the label attached to the hook strand is activated or made detectable by release from the anchor strand, the hook strand with the active/detectable label is re-attached to the support.

In one embodiment, there is provided a method for the detection and/or quantitation of an analyte in a sample, the method comprising: a) providing a support, a capture reagent attached to the support, an anchor strand attached to the support, and a detection reagent linked to a hook strand, wherein the hook strand is releasably linked to the anchor strand by a double-stranded DNA hybrid; b) contacting the support with the sample under conditions that allow simultaneous binding of the capture reagent and the detection reagent to the analyte, to form a tertiary complex; and c) adding a displacer agent attached to a detectable label, wherein the displacer agent is a DNA oligonucleotide complementary to at least a portion of the hook strand and capable of hybridizing to the hook strand, wherein the displacer agent releases the hook strand from the anchor strand via a DNA displacement reaction, such that the detection reagent is released from the support in the absence of the analyte; and d) optionally determining the presence and/or the amount of the detectable label on the support, wherein the presence of the label on the support indicates the presence of the analyte in the sample, and the amount of the label is proportional to the quantity and/or concentration of the analyte in the sample. In some embodiments, the capture reagent and the detection reagent are antibodies, the analyte is an antigen or protein, and the support is a barcoded microparticle. A barcoded microparticle may be, for example, spectrally, graphically, or chemically barcoded.

In a fourth aspect, there is provided a method for preparing a multiplex sandwich assay system, the method comprising: (a) providing a first container comprising a first microparticle, the first microparticle being encoded with a first barcode; (b) attaching the first microparticle to a first capture reagent and a first detection reagent; (c) optionally, storing the first microparticle; (d) providing a second container comprising a second microparticle, the second microparticle being encoded with a second barcode; (e) attaching the second microparticle to a second capture reagent and a second detection reagent; (f) optionally, storing the second microparticle; and (g) mixing the first microparticle and the second microparticle together for use in the multiplex sandwich assay system; wherein the first capture reagent and the first detection reagent are not mixed with the second capture reagent and the second detection reagent prior to attachment to their respective microparticle. The first and the second barcode may be, independently, a spectral, graphical or chemical barcode.

In some embodiments, the respective capture reagent and the respective detection reagent are attached to their respective microparticle at the same time. In other embodiments, the respective capture reagent and the respective detection reagent are attached to their respective microparticle in a two-step reaction, where either the capture reagent or the detection reagent is attached to the microparticle first, followed by subsequent attachment of the other reagent.

In some embodiments, the method further comprises the step of washing the first microparticle and the second microparticle to remove unattached reagents, before mixing them together in step (g). In some embodiments, the method further comprises one or more additional washing step, each step of attaching a capture reagent and/or a detection reagent being followed by a washing step to remove unattached and/or non-specifically attached reagents from the microparticle.

In some embodiments, the microparticle is a bead, e.g., a polystyrene bead. In some embodiments, the microparticle in step (a) is not barcoded, and the method further comprises a step of barcoding the microparticle (e.g., attaching a barcode, such as a fluorescent or luminescent dye(s) or mixture thereof to the microparticle) before step (g), i.e., before mixing a first microparticle and a second microparticle together.

In some embodiments, the first capture reagent, the first detection reagent, the second capture reagent, and the second detection reagent are antibodies.

In an embodiment, there is provided a method of preparing the multiplex sandwich assay system as described herein, the method comprising: (a) providing a support, the support being a planar surface, the surface of a multi-well plate, the surface of a glass plate, or a hydrogel; (b) attaching a first capture reagent to the support at a first position; (c) washing the support to remove unattached first capture reagent; (d) attaching a second capture reagent to the support at a second position; (e) washing the support to remove unattached second capture reagent; (f) attaching a first detection reagent to the support via a first anchor strand attached to the support at the first position; (g) washing the support to remove unattached first detection reagent; (h) attaching a second detection reagent to the support via a second anchor strand attached to the support at the second position; and (i) washing the support to remove unattached second detection reagent; such that whenever the first capture, second capture, first detection, and/or second detection reagents are mixed together, no more than one reagent at a time is not attached to the support.

In some embodiments, methods of preparation of a multiplex sandwich assay system as described herein are advantageous in minimizing cross-reactivity, since the different reagents (capture reagents, detection reagents) are not mixed together in solution before being attached to the support and/or assembled in a biomolecule complex. In this way, non-specific binding of reagents to each other is avoided or at least reduced, in order to minimize cross-reactivity. Undesired background signal or "noise" may also be avoided or at least reduced. In some embodiments, methods are also scalable, allowing rapid and/or cost-effective preparation of multiplex sandwich assay systems. In some embodiments, much less capture and/or detection reagent is needed than for conventional assay systems, which can lead to substantial cost savings for expensive antibody reagents and the like. In some embodiments, less than a nanoliter of an an antibody reagent may be needed to prepare a biomolecule complex, for example.

Other aspects and features of the present invention will become apparent to those ordinarily skilled in the art upon review of the following description of specific embodiments of the invention in conjunction with the accompanying figures.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

For a better understanding of the invention and to show more clearly how it may be carried into effect, reference will now be made by way of example to the accompanying drawings, which illustrate aspects and features according to embodiments of the present invention, and in which.

DETAILED DESCRIPTION

Figure 1:
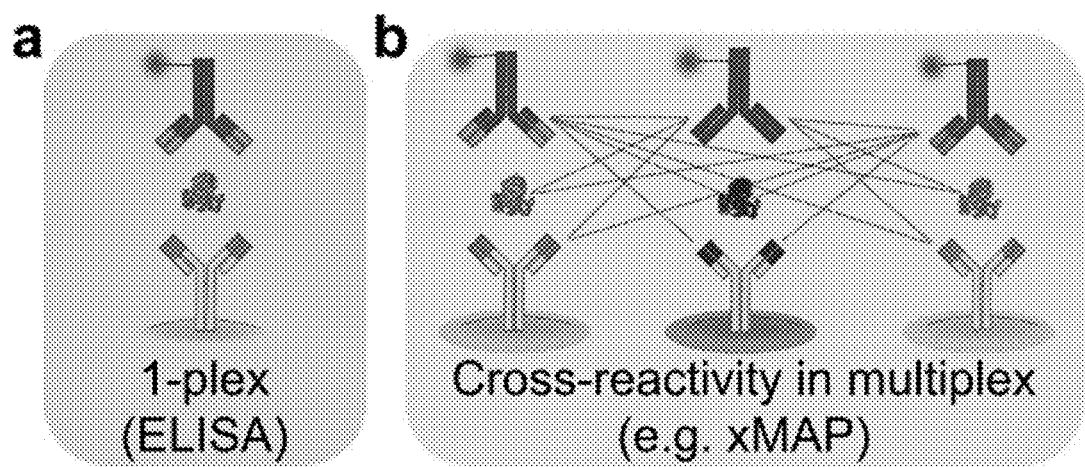
FIG. 1 is a schematic diagram that illustrates in (a) a typical ELISA reaction where only one antibody pair is used (1-plex or singleplex assay); and in (b) cross-reactivity in multiplex analysis produced by non-specific binding events which occur between target biomolecules and mixed AB pairs (depicted as antibody pairs in the figure).

There are provided systems and methods for detecting and/or quantifying one or more analyte using a colocalization-by-linkage assay, as described herein. In particular, there are provided systems and methods having sufficiently low background signal, sufficiently low cross-reactivity between reagents, and/or sufficiently high sensitivity to allow detection and/or quantitation of multiple biomolecules simultaneously in a sample. There are also provided multiplex sandwich assays that are rapid, sensitive, cost-effective, and/or scalable, and methods for their preparation.

It should be understood that this disclosure is not limited to specific devices, systems, methods, or uses or process steps, and as such they may vary.

In order to provide a clear and consistent understanding of the terms used in the present specification, a number of definitions are provided below. Moreover, unless defined otherwise, all technical and scientific terms as used herein have the same meaning as commonly understood to one of ordinary skill in the art to which this invention pertains.

The use of the word "a" or "an" when used in conjunction with the term "comprising" in the claims and/or the specification may mean "one", but it is also consistent with the meaning of "one or more", "at least one", and "one or more than one". Similarly, the word "another" may mean at least a second or more.

As used in this specification and claim(s), the words "comprising" (and any form of comprising, such as "comprise" and "comprises"), "having" (and any form of having, such as "have" and "has"), "including" (and any form of including, such as "include" and "includes") or "containing" (and any form of containing, such as "contain" and "contains"), are inclusive or open-ended and do not exclude additional, unrecited elements or process steps.

As used herein, the term "about" in the context of a given value or range refers to a value or range that is within 20%, preferably within 10%, and more preferably within 5% of the given value or range.

As used herein, the term "and/or" is to be taken as specific disclosure of each of the two specified features or components with or without the other. For example "A and/or B" is to be taken as specific disclosure of each of (i) A, (ii) B and (iii) A and B, just as if each were set out individually herein.

As used herein, the term "support" refers to an immobilizing structure, surface or substrate, such as without limitation a microparticle, a nanoparticle, a well in a plate, a porous polymer, or a hydrogel. It should be understood that the support is not meant to be particularly limited, and any solid, semi-solid, gel or gel-like structure may be used. For example, a support may be an array, a bead (such as without limitation a polystyrene bead), the surface of a multi-well plate (such as a 96-well plate, a 384-well plate, etc.), the surface of a glass slide, a hydrogel matrix, a microfluidic chip, a lateral flow strip, a glass surface, a plastic surface, a silicon surface, a ceramic surface, and the like. In one embodiment, the support is a bead or microparticle or nanoparticle, typically micron-sized or nano-sized, such as without limitation a polystyrene bead, a magnetic bead, a paramagnetic bead, a plastic bead, etc. In another embodiment, the support is a planar microarray. In an embodiment, the support is a nanoparticle. In an embodiment, the support is a microparticle.

As used herein, the term "analyte" refers to a targeted biomolecule or biological cell of interest which is being identified, detected, measured and/or quantified. An analyte may be any biomolecule or biological cell which can be detected using the systems and methods provided herein, such as without limitation proteins, nucleic acids (DNAs, RNAs, etc.), antibodies, antigens, proteins, cells, chemicals, biomarkers, enzymes, polypeptides, amino acids, polymers, carbohydrates, multi-protein complexes, exosomes, oligonucleotides, low molecular weight compounds, and the like. Non-limiting examples of analytes include antibodies, antibody fragments (e.g., scFv, Fab, etc.), aptamers, modified aptamers, somamers, affimers, antigens, proteins, polypeptides, multi-protein complexes, exosomes, oligonucleotides, and low molecular weight compounds.

As used herein, a "sample" refers to any fluid or liquid sample which is being analyzed in order to detect and/or quantify an analyte. In some embodiments, a sample is a biological sample. Examples of samples include without limitation a bodily fluid, an extract, a solution containing proteins and/or DNA, a cell extract, a cell lysate, or a tissue lysate. Non-limiting examples of bodily fluids include urine, saliva, blood, serum, plasma, cerebrospinal fluid, tears, semen, sweat, pleural effusion, liquified fecal matter, and lacrimal gland secretion.

As used herein, the term "encoded microparticle" refers to a microparticle that is barcoded, e.g., encoded spectrally according to either the target analyte or the specific test that is to be performed in the assay. Barcoded (or encoded) microparticles are often used in multiplexed suspension assays as they allow particles in a large mixture to be distinguished. The method of barcoding is not particularly limited. Barcoding can be performed using, for example, spectral, graphical, or chemical means. For example, spectral encoding of microparticles can be performed by labeling the microparticles with precise proportions of multicolor dyes. This approach allows simple and high throughput read-out by flow cytometry. As another example, graphically barcoded microparticles are typically engraved or otherwise patterned with a visual pattern that can be characterized via microscopy. Microparticles can also be chemically barcoded, for example using unique DNA sequences that can later be detected via DNA detection means.

As used herein, the term "non-specific binding" refers to an unintended reaction between reagents and/or molecules within the sample, including but not limited to reaction between non-cognate antibodies and protein sticking through hydrophobic interactions.

As used herein, the terms "affinity binder" (AB), "binder", and "reactant" are used interchangeably to mean any molecule capable of specifically recognizing a target analyte, e.g., via a non-covalent interaction. Examples of affinity binders (ABs) include without limitation immunoglobulin-G (IgG) antibodies (e.g., whole molecules or Fab fragments), aptamers, affimers, nanobodies, ankyrins, and single-chain variable fragments (scFvs).

As used herein, the term "sandwich assay" is used to mean an analyte-targeting assay wherein two ABs simultaneously bind the target analyte of interest and can be used to detect and/or quantify it.

As used herein, the terms "multiplex sandwich assay", "multiplexed sandwich assay" and "MSA" are used interchangeably to mean a sandwich assay that targets multiple (e.g., two or more) analytes from the same sample and/or assay volume at the same time, multiple AB pairs being used in the assay system at the same time.

As used herein, the term "cross-reactivity" is used to mean a particular case of non-specific binding or non-specific reaction in a multiplexed sandwich assay, wherein an unintended complex is formed that includes non-cognate affinity binders, e.g., as shown in FIG. 1.

As used herein, the terms "capture affinity binder", "cAB", "capture AB", "capture binder" and "capture reagent" are used interchangeably to refer to an AB that is attached to a support in a biomolecule complex and is not released from it. A capture AB may be attached directly to a support (e.g., via a covalent bond, a biotin-streptavidin bond, a DNA oligonucleotide linker, or a polymer linker) or indirectly (e.g., via linkage to an an anchor strand, e.g., by conjugation or through a linker such as a capture strand). Non-limiting examples of capture reagents include antibodies, antibody fragments (e.g., scFv, Fab, etc.), aptamers, modified aptamers (such as slow off-rate modified aptamers or somamers), affimers, antigens, proteins, polypeptides, multi-protein complexes, exosomes, oligonucleotides, and low molecular weight compounds.

The term "capture strand" refers to a linker (e.g., an oligonucleotide, a polymer, etc.) that links a capture reagent to an anchor strand (and hence the support to which the anchor strand is attached).

As used herein, the terms "detection affinity binder", "dAB", "detection AB", "detection binder" and "detection reagent" are used interchangeably to refer to an AB in a biomolecule complex that is releasably attached to a support. The dAB is generally used for signal transduction and assay signalling. In some embodiments of methods and systems provided herein, for example, the fraction of dAB unbound to an analyte is released from the support such that no signal is produced in the absence of bound analyte. In some embodiments, the dAB is bound to a label or means for signal transduction and assay signalling. Non-limiting examples of detection reagents include antibodies, antibody fragments (e.g., scFv, Fab, etc.), aptamers, modified aptamers, somamers, affimers, antigens, proteins, polypeptides, multi-protein complexes, exosomes, oligonucleotides, and low molecular weight compounds.

As used herein, the term "anchor strand" refers to a linker that attaches to an immobile point on a support. Non-limiting examples of anchor strands include polymers, such as polyethylene glycol (PEG), oligonucleotides (such as a single-stranded DNA oligonucleotide, a single-stranded RNA oligonucleotide, or a double-stranded DNA or RNA oligonucleotide, or a DNA-RNA hybrid), and oligosaccharides.

As used herein, the term "hook strand" refers to a linker that links a detection AB to an anchor strand and hence attaches it to a support. The hook strand is typically attached releasably to the anchor strand, e.g., in such a way that the attachment can be released. Generally, when the attachment between the hook strand and the anchor strand is released, the fraction of detection AB linked to the hook strand that is not bound to a target analyte will be released from the anchor strand, and therefore also released from the support, such that no signal from the detection AB can be detected on the support in the absence of the target analyte. In this way, signal on the support is only detected when the target analyte is present and bound by the detection AB and the capture AB.

In some embodiments, where a label is on the hook strand and/or the detection reagent and is only activated or detectable after the release of the hook strand and/or the detection reagent from the anchor strand, the signal is "release-dependent", as it will only be detectable after the release of the hook strand and/or the detection reagent from the anchor strand. Similarly, in some embodiments, where the label is on a displacer agent hybridizing to the hook strand, the signal is "displacement-dependent".

As used herein, the term "displacer agent" refers to an agent that directly or indirectly causes or initiates release of the releasable linkage between the anchor strand and the hook strand, thereby releasing the hook strand (and the detection AB linked thereto) from the support. The mechanism used by the displacer agent is not particularly limited. For example, the displacer agent may directly or indirectly cause or initiate cleavage, displacement, or unbinding of the linkage between the anchor strand and the hook strand; other mechanisms are possible and are also contemplated. In some embodiments, the hook strand is displaced from the anchor strand using a DNA oligonucleotide that hybridizes to the hook strand and/or the anchor strand. Examples of displacer agents include but are not limited to a displacement DNA oligonucleotide, a source of mono- or poly-chromatic light, a restriction enzyme, and a reducing agent such as dithiothreitol (DTT). In some embodiments, where photocleavable DNA segments are used, the displacer agent may be a light which effects release via a photocleavage reaction. In some embodiments, the displacer agent is labeled, e.g., with a dye, a fluorophore, a specific DNA sequence, an enzyme, a biotin moiety, and the like. When the displacer agent is labeled, it can serve the dual-function of releasing the hook strand and labelling it simultaneously.

As used herein, the term "label" refers to any molecule or a portion of a molecule that generates a signal, can be targeted with a signal-generating molecule, or is otherwise detectable. Examples of labels include but are not limited to biotin, fluorophores, enzymes, enzyme substrates, and specific DNA sequences. An "inactive" or "undetectable" label refers to a label which is not active, is masked, or is otherwise undetectable, e.g., not capable of generating a detectable signal, such as without limitation a quenched fluorescent dye.

It should be understood that systems and methods provided herein can be used in virtually any type of sandwich assay wherein two sets of ABs are used. However, for simplicity, specific embodiments of the present invention are presented herein using whole-molecule Immunoglobulin-G antibodies (IgG) as ABs, which represents one of many possible embodiments. It should be understood that antibodies are not limited to whole-molecule IgG and that many different antibodies, antibody fragments, etc. can be used. Further, ABs are not limited to antibodies. Similarly, many different types of sandwich assays other than the specific ones described herein can be used.

Figure 4:
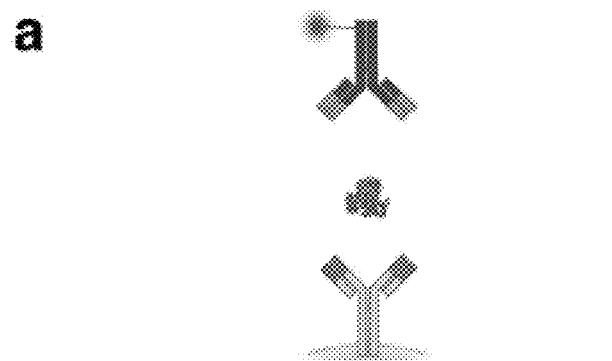
FIG. 4 shows a schematic diagram that illustrates in (a) a typical ELISA reaction where only one antibody pair is used (1-plex or singleplex assay); and in (b) cross-reactivity in multiplex analysis produced by non-specific binding events which occur between target biomolecules and mixed AB pairs (depicted as antibody pairs in the figure). (c) shows a CLA system in which cross-reactivity is prevented by colocalizing antibody pairs on individual beads using DNA linkages.
Figure 4:
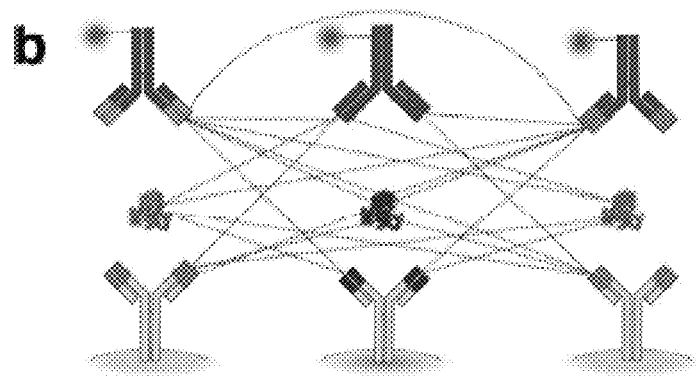
Figure 4:
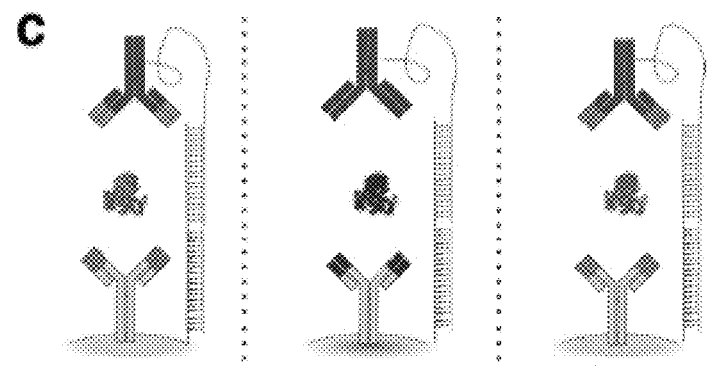

In some embodiments, there is provided a dual-AB or sandwich assay that can avoid cross-reactivity by colocalizing two ABs (a capture AB and a detection AB) on a support prior to exposure to a biological sample containing an analyte of interest. Colocalization on the support does not permit any mixing of different AB pairs prior to exposure to the analyte, and can thus reduce or eliminate cross-reactivity between reagents and/or background (such as that shown in FIG. 1 or FIG. 4). In an embodiment, there is provided a support attached to a mixture of capture and detection ABs, where each set of capture and detection ABs is capable of binding with an analyte of interest, with the detection AB attached to the support, optionally via a releasable linker. In an embodiment, there is provided a support attached to a mixture of capture and detection ABs, wherein each analyte is capable of binding simultaneously to both a capture AB and a detection AB, and wherein the detection AB is releasably attached to the support, optionally via a releasable hook strand. Upon release of the detection reagent and/or the hook strand, the corresponding detection AB remains on the support only if bound to the analyte in a tertiary complex with a capture AB.

It should be understood that "linkers" and "strands" used in methods and systems provided herein are not particularly limited. Non-limiting examples of linkers and strands include DNA oligonucleotides (also referred to as DNA oligos), polymers, polysaccharides, and the like. DNA linkages can be covalent, such as conjugation between a hook strand oligo and a detection AB, or non-covalent, such as hybridization or base-stacking between two complementary DNA sequences. To allow formation of a capture AB-antigen-detection AB tertiary complex, the hook strand is designed to have a flexible, single-stranded portion. Displacement of a DNA linkage can be performed using several methods including but not limited to a toe-hold mediated DNA displacement reaction, enzymatic cleavage, and photo-activated cleavage. Specific DNA sequences can also be used as labels, which can be either directly targeted using a complementary sequence that is fluorescently labeled, can be used as amplification triggers or primers through a hybridization-chain reaction or a polymerase-chain reaction, and can be read-out via sequencing.

It should be understood that "oligonucleotides" (also referred to as "oligos") used in methods and systems provided herein are not particularly limited. For example, oligos can be modified using fluorescent dyes on 5' or 3' termini, modified with a photocleavable phosphodiester back-bone, conjugated to a protein, a biotin, or an enzyme, etc.

These embodiments may also be referred to herein as a "Colocalization-by-Linkage Assay" or "CLA". In some embodiments of CLA, the detection AB is labeled (i.e., attached to a label). In some embodiments of CLA, the hook strand linking the detection AB to the anchor strand is labeled (i.e., attached to a label). Generally the label attached to the detection AB or the hook strand is inactive or undetectable, such that the label can be detected after release of the detection AB from the support (i.e., after the hook strand is released from the anchor strand). Signal detection from the label is thus release-dependent (also referred to, in some embodiments, as "displacement-dependent"). In this way, only detection ABs bound to the analyte in a tertiary complex with a capture AB and released from the anchor strand will be detected, as unbound detection AB will be released from the support (and can be removed e.g., by washing). Background signal may also be reduced since the label is inactive or undetectable prior to release, or if a given hook strand is not released (i.e., due to the release-dependent or displacement-dependent nature of the signal). In some embodiments, therefore, methods and systems provided herein may be referred to as "release-dependent transduction" (or "RDT") or "displacement-dependent detection", to reflect the release-dependent (or displacement-dependent) signal transduction.

Conventional sandwich assays generally rely on the presence of detection ABs to transduce a signal and detect the presence of an analyte. Similarly, in certain embodiments of systems and methods presented herein, the detection AB and/or the hook strand can act as signal transducers. However, in contrast to conventional assays, in systems and methods provided herein the detection AB and/or the hook strand optionally linked thereto can remain on the support only when a tertiary complex is formed with the analyte and the capture AB. It will be appreciated that, if the detection reagent and/or the hook strand is not successfully or completely released from the anchor strand, then it can remain on the support even in the absence of the analyte. In this case, if the detection AB and/or the hook strand is attached to a label that is active or detectable even when attached to the anchor strand, then any non-released, labeled detection AB and/or hook strand would transduce a signal. In other words, in that case, any labeled and non-released detection reagent and/or hook strand could result in a signal independent of the presence of the analyte, contributing to non-specific background signal, and reducing assay performance and/or sensitivity. It will be appreciated that the background signal in that case will be proportional to the fraction of non-released detection reagents and/or hook strands. It should also be appreciated that near-complete release of complexes from supports may be difficult to achieve due to steric hindrance, sticking, and/or incomplete washing. However, release-dependent transduction (RDT) can minimize or eliminate these problems, as no signal transduction occurs if the release of the detection reagent and/or the hook strand from the anchor strand is not complete, as demonstrated in FIG. 24.

In some embodiments, therefore, systems and methods provided herein include an additional level of redundancy to reduce background signal and/or increase sensitivity by the use of release-dependent transduction (RDT). In RDT, signal transduction occurs only if both of the following conditions are satisfied: (i) formation of a tertiary capture AB-analyte-detection AB complex, and (ii) release of the corresponding detection AB and/or hook strand from the anchor strand. In such cases, a non-released detection AB and/or hook strand will not contribute to the background signal. This signal transduction mechanism, which we herein refer to as "release-dependent transduction (RDT)", can be achieved through various means. For example, some embodiments can include a label on the hook strand, wherein the label is inactive or undetectable until after the release from the anchor strand, such that a non-released (e.g., non-displaced) hook strand and/or detection AB) will not contribute to or transduce the signal.

In some embodiments of RDT, a hook strand is labeled with a fluorescent dye quenched by a quencher on the anchor or another proximal strand, such that release results in unquenching or activation of the fluorescent dye.

In some embodiments of RDT, the detection reagent and the hook strand are not labeled, and instead the displacer agent is labeled. In this case, the displacer agent hybridizes to the hook strand, displacing it from the anchor strand, and simultaneously labeling it. If the detection AB is not bound to analyte and capture AB in a tertiary complex, then the hook strand, the displacer agent, and the label are washed off the support. Since the label is attached to the displacer agent, the label is only present on the support when both conditions are met: (i) release or displacement from the anchor strand has occurred, and (ii) analyte has bound to both capture and detection ABs (shown in FIG. 7, for example).

It will be appreciated that other embodiments of RDT are possible, and the mechanism of RDT is not meant to be particularly limited.

Figure 6:
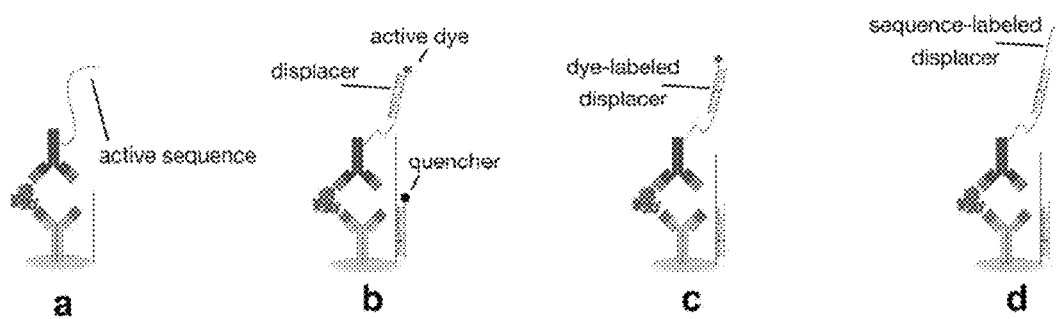
FIG. 6 shows a schematic diagram illustrating exemplary embodiments of detection CLA in the presence of the analyte, after a successful displacement reaction. (a) Label is a specific DNA sequence on the hook strand that can be targeted via DNA hybridization for detection. (b) Displacer agent is used to release hook strand oligo from the anchor strand, resulting in activation of the label attached to the hook strand (in this case, unquenching of a dye after release). (c) Dye-labeled displacer agent binds preferentially to the hook strand oligo, releasing it from the anchor strand, and simultaneously labeling both the hook strand and the bound tertiary complex. (d) Sequence-labeled displacer agent binds preferentially to the hook strand oligo, releasing it from the anchor strand, and simultaneously labeling both the hook strand and the bound tertiary complex.

In some embodiments of RDT, the detection AB or the anchor strand is attached to a label. In some embodiments, the hook strand linking the detection AB to the anchor strand is labeled (i.e., attached to a label). Generally the label attached to the detection AB, the anchor strand, or the hook strand is inactive or undetectable, such that the label can only be detected after release of the detection AB from the support (i.e., after the hook strand is released from the anchor strand, as shown for example in FIG. 6). In this way, the only detection AB-hook oligo complexes that are detected are the ones with a detection AB bound to the analyte in a tertiary complex with a capture AB and a hook strand successfully released from the anchor strand. Otherwise, unbound detection AB will be released from the support (and can be removed e.g., by washing), and all non-released strands are not detected, whether or not the analyte was bound. In this way, background signal from non-released detection ABs and/or hook strands is mitigated, ensuring a low background signal and/or high sensitivity detection.

In other embodiments of RDT, the hook strand contains a label that remains inactive or undetectable until the hook strand is released from the anchor strand. For example, this can be achieved when the hook strand and the anchor strand are DNA oligonucleotides bound together via hybridization, wherein the hook strand contains a DNA sequence label normally hybridized to the anchor strand and hence unavailable for binding, or undetectable. Release of the hook strand oligo from the anchor strand oligo reveals a detectable label on the hook strand. Such release can be achieved e.g., via enzymatic cleavage, DNA displacement, or photocleavage using light.

In some such embodiments, there is provided a release or displacer agent which is an oligonucleotide that displaces the anchor strand-hook strand hybrid by binding to the anchor strand oligo via a toe-hold displacement reaction. In an embodiment, the hook strand and the detection AB are both not labeled, and a labeled displacer agent (e.g., a fluorescently-labeled oligonucleotide) performs RDT through the dual-function of release (displacement) and labeling. In this way, through only labeling the displaced hook strands, a detectable signal/signal transduction only occurs on a support when two conditions are met (displacement of the hook strand and presence of the analyte), akin to an "AND" logical gate (shown in FIG. 7B, for example).

In some embodiments of assays and systems provided herein, one or more set of capture and detection ABs is attached to a support, each set being specific for an analyte of interest. In this way, the capture and the detection AB are pre-assembled and colocalized on the support, prior to exposure to a biological sample containing the analyte of interest. As described above, the detection AB is attached to the support releasably. In some embodiments, the detection AB is attached to the support by a releasable linker (a hook strand) which is linked to an anchor strand attached to the support. The hook strand is generally flexible and allows the detection AB to diffuse freely within the bounds allowed by the lengths of the hook strand and/or the anchor strand. The hook strand and the releasable link are not particularly limited and may vary in size, flexibility, structure, etc., as long as they allow simultaneous binding of the analyte by the detection AB and the capture AB. The capture AB and the detection AB generally bind separate regions of the analyte, although they may bind overlapping sites, as long as they are capable of binding the analyte simultaneously.

In some embodiments, the detection AB is linked to the support using a hook strand which is a DNA oligonucleotide that can bind specifically to the anchor strand attached to the support. After contacting and incubating with the biological sample (i.e., target recognition step), the detection AB is separated from the anchor strand by breaking the linkage between the hook strand and the anchor strand on the surface. This release the fraction of detection AB that has not formed a tertiary capture AB-analyte-detection AB complex. It should be understood that the linkage between the hook strand and the anchor strand may be released or broken in several ways, such as without limitation DNA strand displacement, enzymatic cleavage, photo-activated cleavage, and the like.

As encompassed herein, many ABs targeting many different analytes can be mixed in the same assay volume (i.e., multiplexing); interaction between different ABs on different supports (or between different ABs on different locations/positions on the same support) are limited by the linkages to the support(s), so that interaction between ABs from different supports/locations is avoided. This is in contrast to conventional multiplexing technologies that can not limit interactions between ABs when all ABs are mixed in solution. Further, with methods and systems described herein, different microparticle populations can be fabricated separately in large batches, each containing a different AB capture-detection pair needed to detect a specific antigen, ensuring that cross-reactivity does not occur during manufacturing.

In some embodiments, multiplexed CLA methods and systems can thus avoid the cross-reactivity scenarios shown in FIG.1. For example, as will be appreciated by those skilled in the art, the colocalization of cognate capture and detection ABs on their respective supports (e.g., microparticles) will eliminate unwanted interactions such as, for example, binding between non-cognate detection and capture ABs. In addition to those scenarios shown in FIG.1, those skilled in the art will recognize that, as opposed to conventional multiplexed sandwich assays, analytes that indiscriminately bind, or stick, to off-target supports cannot be detected by their cognate detection AB in methods and systems provided herein, and hence do not contribute to increase the background signal.

In some embodiments, on each support, the local concentrations of the capture and detection ABs can be high, which can serve to concentrate the analytes and increase the sensitivity. On the other hand, the total concentration of each capture and detection AB in the entire assay volume is only dependent on the concentration of target-specific supports (e.g., microparticles, microarray spots) and can be designed to yield low bulk-concentrations of detection ABs upon release. For example, while the local-concentrations can be in the micromolar range, the use of a low number of target-specific microparticles can yield bulk detection AB concentrations too low (<pM) to yield any off-target binding, as shown for example in FIG. 22. The bulk concentrations can be further decreased by increasing the volume during the release step. Thus, in certain embodiments, methods and systems provided herein can further avoid cross-reactivity that occurs after detection AB release, due to the low concentration or amount of detection AB used on the support.

In some embodiments, simultaneous binding of two colocalized binders (capture AB, detection AB) to two different epitopes of the same analyte (that is, increased binding avidity) can result in a much lower effective off-rate (koff) in comparison to conventional sandwich assays where capture and detection ABs are added sequentially. After sample introduction and incubation, the supports in methods and systems provided herein can be stringently washed, since the analytes are bound with high avidity. Hence, in some embodiments of methods and systems provided herein, stringent washing can be used to reduce assay background and/or improve sensitivity and/or specificity. In some embodiments, it may be desirable to rapidly execute the assay steps following the release of a hook strand from an anchor strand and up until read-out of the assay signal, since off-binding of analytes can result in a reduced signal which can contribute to reduced sensitivity, although such effects are generally reduced in CLA.

In one embodiment of methods and systems provided herein, a support is an encoded micron-sized microparticle, and capture reagent and the detection reagent are both antibodies, wherein the capture reagent and its cognate detection reagent are colocalized on the surface of the same support using DNA linkages (in other words, the hook strand and the anchor strands are single-stranded DNA oligonucleotides, linked together via a double-stranded DNA hybrid). In some such embodiments, the detection reagent linked to the hook strand and the anchor strand are homogeneously mixed and attached to the surface of the microparticle, wherein the anchor strand is linked to the hook strand through partial hybridization, the hook strand being conjugated to the detection reagent, the hook strand being a flexible and releasable DNA linker. The hybrid between the anchor and hook strands is generally stable during conditions of sample incubation. In some embodiments, the capture reagent is also linked to the microparticle via a DNA linker as well. In some such embodiments, release of the hook strand from the anchor strand can be performed via a toe-hold mediated DNA displacement reaction. In such embodiments, a displacer agent is an oligonucleotide designed to bind to a toe-hold sequence on the hook strand to drive the displacement reaction forward. In some such embodiments, release of the hook strand from the anchor strand can be performed without a displacer agent, e.g., by raising the temperature so that the DNA hybrid "melts" or is unbound.

In an embodiment, a detection AB and/or a hook strand is labeled, e.g., with a dye, a biotin moiety that can be detected using a fluorescently-labeled streptavidin in a subsequent step etc. In certain embodiments, a detection AB can be detected after binding an analyte with a labeled-binder, for example, an IgG can be targeted using a labeled species-specific secondary-IgG. In some embodiments, the detection AB and the hook strand are not labeled, and instead a displacer agent used to release the hook strand from the anchor strand is labeled. In such embodiments, the labeled displacer agent attaches to the hook strand and/or the detection AB after the release of the hooks strand from the anchor strand.

In some embodiments, the label is a specific DNA sequence that can be detected or targeted in a subsequent step(s). For example, a specific DNA sequence can be targeted with a subsequent DNA hybridization step that labels it with a dye. In an embodiment, the specific DNA sequence is detected and amplified through Polymerase Chain Reaction (PCR) or other enzymatic DNA amplification means. Specific DNA sequences can also be cleaved and detected by other means such as sequencing. Embodiments using DNA sequence as a label are not limited and may include the sequence being part of the hook strand (and hence, initially inactive/undetectable), or present on the displacer agent (shown for example in FIG. 6A, D).

In some embodiments, there is provided a detection AB linked to a hook strand and attached to a microparticle indirectly via a releasable link to an anchor strand attached thereto. The hook strand is partially complementary to the anchor strand attached to the microparticle. The anchor strand may be attached to the microparticle via for example a streptavidin/biotin interaction or a chemical bond. The detection AB is thus attached to the microparticle. In this embodiment there is further provided a capture AB which is attached to the microparticle surface, and wherein the detection AB recognizes the same antigen as the capture AB and both ABs can bind the antigen simultaneously. In addition, there is provided a displacement oligonucleotide (the displacer agent) that has a sequence that is complementary to the hook strand, overlapping with the sequence of the anchor strand, so that the detection AB is released from the anchor strand and thus released from the microparticle, if no antigen is bound (i.e., if there is no tertiary complex between capture AB-antigen-detection AB). In a further embodiment, there is also provided a fluorescently-labeled secondary antibody that binds to the detection AB remaining on the microparticle after the displacement reaction.

Figure 15:
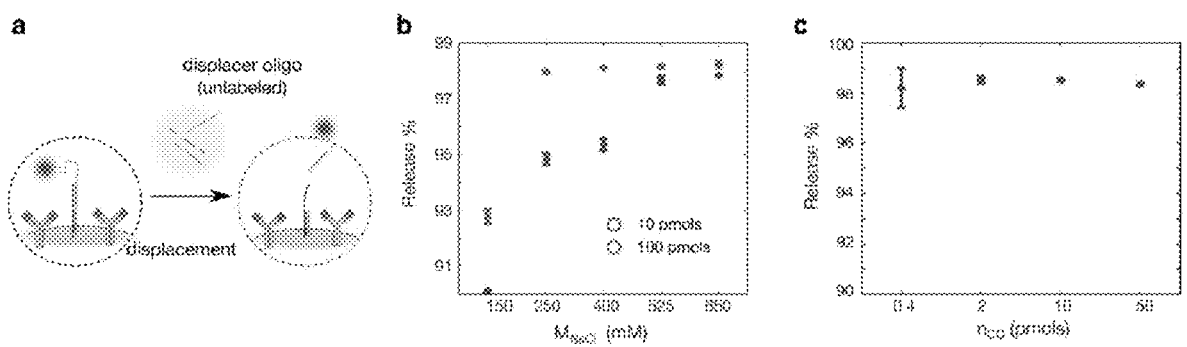
FIG. 15. shows optimization of toe-hold mediated displacement efficiency. (a) Illustration of the displacement reaction, wherein Cy5-labeled HOs are displaced using unlabeled DOs. (b) Release efficiency with respect to increasing NaCl concentration (x-axis) for varying CO starting amounts (blue and red for for nco=10 pmols, nco=100 pmols, respectively). No SOs were used in this experiment (i.e. nso=0 pmols). The release efficiency was calculated as $(I_0-I_f)/(I_0-I_B)$ where $I_0$, $I_f$, and $I_B$ are the fluorescence before release, after release, and of the background, respectively. The release efficiency was significantly improved at increased ionic strengths. Increased density of COs led to increased release efficiency, which may be ascribed to reduced fraction of non-specifically bound oligos. (c) Release efficiency with respect to CO density at high salt concentrations (500 mM of NaCl).
Figure 24:
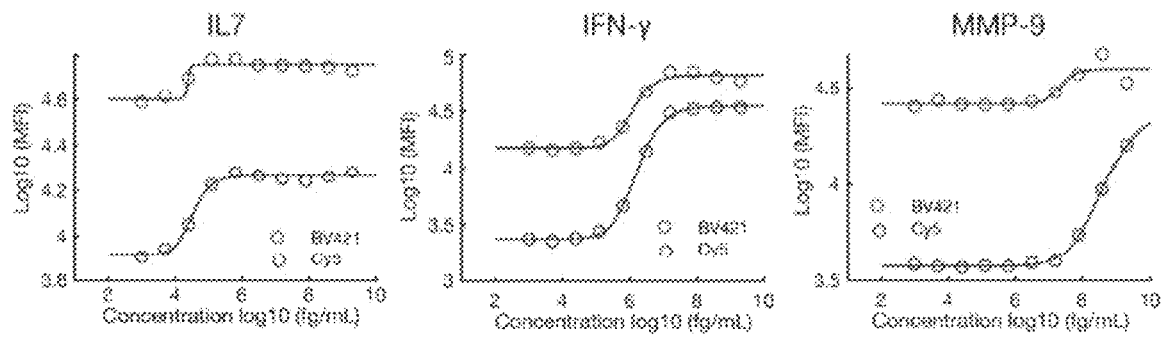
FIG. 24 shows calibration curves obtained using two labelling methods: direct detection of dAbs using BV421-labelled secondary antibody, and displacement-dependent detection using a Cy5-labelled displacer oligo. Calibration curves for IL-7, FN-gamma, and MMP-9 were performed in buffer (PBST) by spiking protein standards in decreased concentrations, and running the assay as described.

It should be noted that, in embodiments where capture and detection ABs are pre-assembled on a support, and detection ABs are labeled with a detectable label, any non-released hook strand-detection AB complexes will result in an analyte-independent signal, which could contribute to the background noise (as shown in FIG. 24). Hence, it will be appreciated that to avoid increasing the background signal, a near-complete anchor strand-hook strand displacement reaction and washing of hook strand-detection AB complexes are necessitated. It will also be appreciated that such near-complete release can be difficult even with optimized conditions (FIG. 15). To reduce such increased background signal resulting from inefficient release of the anchor strand-hook strand link, in some embodiments, the hook strand, anchor strand, or detection ABs are labeled with a label that remains inactive/undetectable until displacement or release of the hook strand from the anchor strand. In another embodiment, the hook strand, anchor strand, or detection ABs are not labeled, and the displacer agent is labeled with a detectable label. In such embodiments, signal transduction at the support only occurs if both of the following conditions are satisfied: (i) formation of a tertiary captureAB-analyte-detectionAB complex, and (ii) displacement of the hook strand-anchor strand hybrid. In these embodiments, a non-displaced hook strand will not contribute to the signal. It should be appreciated that, similarly, embodiments where the label on the detection AB and/or the hook strand is inactive or undetectable until after the release can be advantageous since a non-released (e.g., non-displaced) hook strand (or detection AB) will not contribute to the signal.

Figure 23:
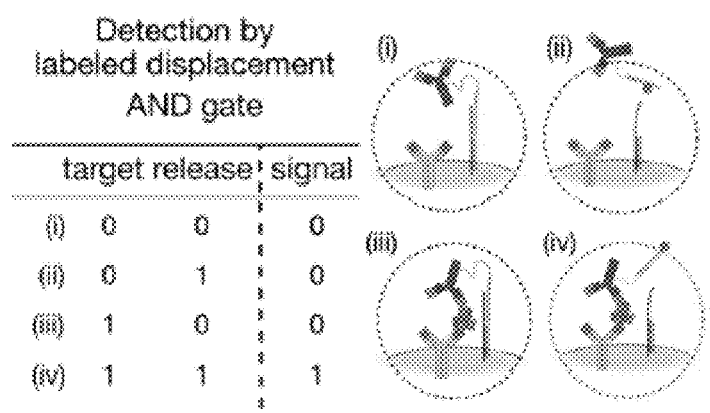
FIG. 23 shows an AND (Boolean) logic gate representation of the detection by labeled-displacement step, where detection at the single-molecule level requires both the capture of target and successful hook strand oligonucleotide (HO) release.

In one embodiment, a labeled displacer agent (e.g., oligonucleotide) can perform the dual-function of release (displacement) and labeling. In this way, through only labeling the displaced hook strands, a detectable signal/signal transduction necessitates two conditions, akin to an "AND" logical gate (FIG. 23). One potential advantage of such embodiments is that they do not require a change in the design of DNA sequences or linkage properties of the detection complex including hook and anchor strands.

In some embodiments, an additional level of redundancy can be achieved by using a hook strand with an inactive or undetectable label which is only activated or detectable upon displacement from the anchor strand. For example, in one embodiment a hook strand is labeled with a dye that is quenched by a dye quencher that can be conjugated to the anchor strand. In another embodiment, displacement can be similarly achieved using a restriction enzyme, followed by signal generation using a labeled-oligo that targets the previously-hybridized (and hence unavailable for binding) portion of the hook strand, thereby only hybridizing to and labeling already displaced hook strands.

In certain embodiments, there is provided a detection AB linked to a microparticle via a hook strand, the hook strand being an oligo, which is linked to the detection AB. The hook strand oligo is partially complementary to an anchor strand, which is also an oligo, linked to the microparticle via e.g., a streptavidin/biotin interaction or a chemical bond, thus attaching the detection AB to the microparticle. There is further provided a capture AB which is linked to the microparticle surface and wherein the detection AB recognizes the same antigen as the capture AB and both ABs can bind the antigen simultaneously. In addition, there may be provided a displacement agent which is an oligonucleotide containing a fluorescent label or a DNA barcode sequence and has a sequence complementary to the hook strand oligonucleotide, overlapping with the sequence of the anchor strand oligonucleotide so that the detection Ab is released from the anchor strand oligo and thus may be released from the microparticle.

It should be understood that, in methods and systems provided herein, the use of colocalization and linkages may necessitate rational topological design to optimize the availability of both ABs (capture AB and detection AB) across a support. In some embodiments, with stochastically distributed capture ABs and/or detection ABs attached to the support, appropriate binding of an analyte may require optimization of two important design parameters: (i) the relative density of the capture and detection ABs, and (ii) the length of the hook strand. These two parameters serve to control the time-averaged distance between capture and detection ABs by considering the gyration radius of the detection AB. In some cases, the distance between capture and detection ABs, and ultimately the effective-affinity at the single-molecule level, may be stochastic and difficult to control. Therefore, in some embodiments it may be desirable to optimize the aforementioned two parameters for optimal assay performance.

Figure 5:
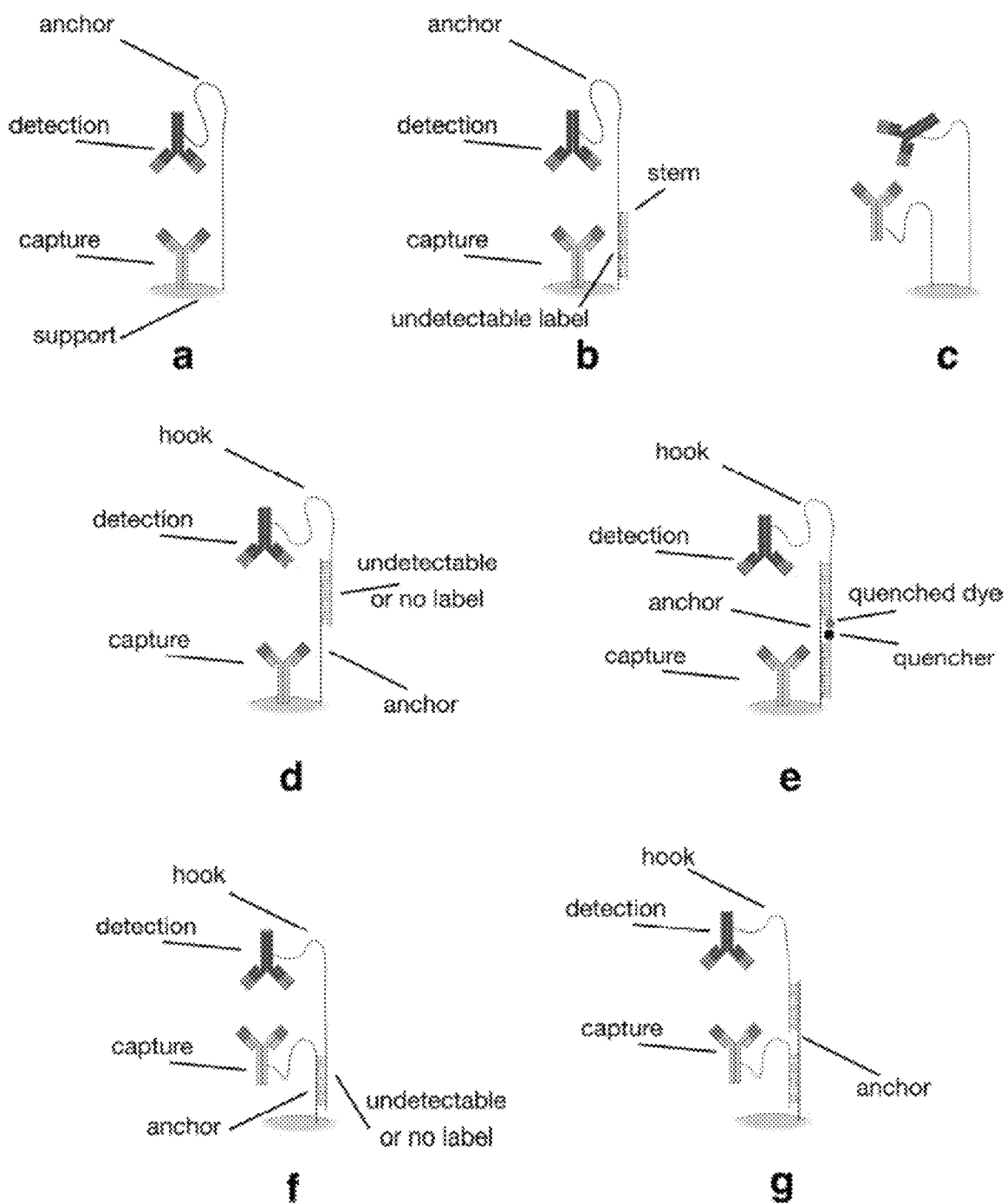
FIG. 5 shows a schematic diagram illustrating exemplary embodiments of CLA complexes prior to contact with a biological sample and displacement, wherein the label is either absent or inactive/undetectable. (a) Detection AB is linked to the support using the anchor strand (i.e., direct linkage to the anchor strand). (b) A stem oligo hybridizes to the anchor strand, which is labeled, and serves to mask the label (e.g., a specific DNA sequence) so that it is undetectable before release. (c) Both capture and detection antibodies are flexibly linked to the support. (d) Detection AB is linked to a hook strand, the hook strand being releasably attached to the anchor strand, optionally including an undetectable label (the label may be attached to the hook strand or to the anchor strand). (e) Detection AB is linked to a hook strand, the hook strand being releasably attached to the anchor strand, and the hook strand is conjugated to a dye that is quenched (before release) by a proximal quencher on a stem oligo that is also bound to the anchor strand. (f) Both capture and detection antibodies are linked to the anchor strand, the capture AB being linked directly to the anchor strand, and the detection AB being attached indirectly via a hook strand oligo that is optionally attached to an undetectable label (i.e., label is undetectable when hook strand is attached to the anchor strand, and becomes detectable after release). (g) Both capture and detection antibodies are linked indirectly to the anchor strand via their respective capture and hook strands.
Figure 21:
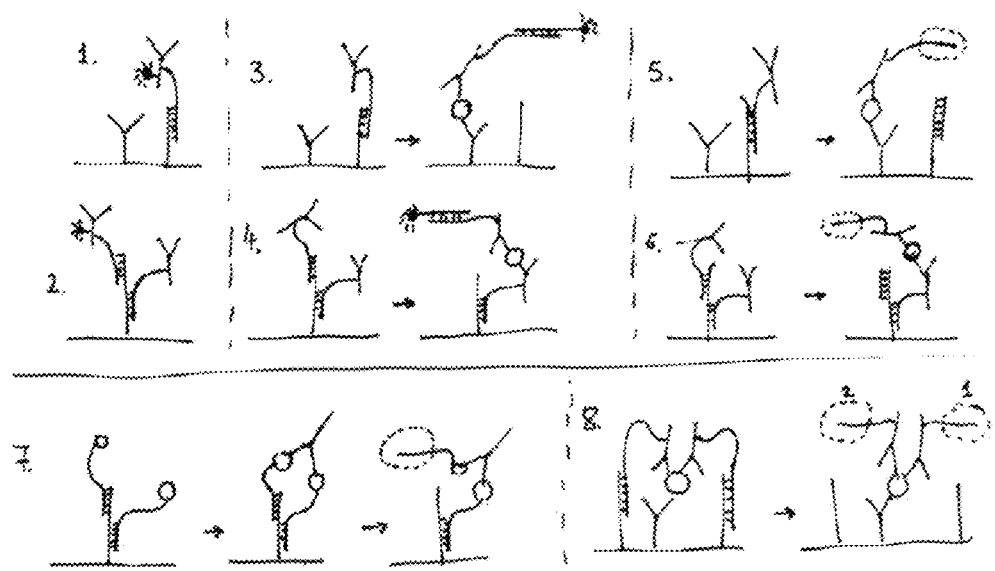
FIG. 21 shows a schematic illustration of several embodiments. (1) shows a CLAMP embodiment where the capture and detection reagents are antibodies and the detection reagent is linked to the anchor strand by a DNA hybrid, and the detection antibody is labelled; (2) shows an embodiment where both capture and detection antibodies are attached to the anchor strand via an oligo linker and a DNA hybrid, and the detection antibody is labelled. (3) shows an embodiment where shows a CLAMP embodiment where the capture and detection reagents are antibodies and the detection reagent is linked to the anchor strand by a DNA hybrid, and there is no label on the detection reagent or the hook strand. A tertiary complex forms in the presence of analyte, and the hook strand is displaced from the anchor strand by a labeled displacer oligo. (4) shows an embodiment where both capture and detection antibodies are attached to the anchor strand via an oligo linker and a DNA hybrid and there is no label on the detection reagent or the hook strand. A tertiary complex forms in the presence of analyte, and the hook strand is displaced from the anchor strand by a labeled displacer oligo. (5) shows the embodiment of (1) but where the label is attached to the hook strand and is masked by the DNA hybrid attaching the hook strand to the anchor strand. A tertiary complex forms in the presence of analyte, and the hook strand is displaced from the anchor strand by a displacer oligo that binds or hybridizes to the anchor strand. The label on the hook strand is activated or unmasked after the displacement reaction. (6) shows the embodiment of (4) but where, as in (5), the label is attached to the hook strand and is masked by the DNA hybrid attaching the hook strand to the anchor strand. A tertiary complex forms in the presence of analyte, and the hook strand is displaced from the anchor strand by a displacer oligo that binds or hybridizes to the anchor strand. The label on the hook strand is activated or unmasked after the displacement reaction. (7) shows an embodiment where the capture and detection reagents are both antigens and are both linked to the anchor strand via an oligo linker that hybridizes to the anchor strand. A complex is formed in the presence of an antibody (the analyte in this embodiment) that binds both antigens. The label is attached to the hook strand and is masked by the DNA hybrid attaching the hook strand to the anchor strand. The label on the hook strand is activated or unmasked after cleavage from the anchor strand. (8) shows an embodiment where the capture reagent is an antibody attached directly to the support and there are two anchor strands. Each of the two anchor strands is linked by a DNA hybrid to a detection antibody. In the presence of analyte a quaternary complex is formed. Each of the two hook strands is labeled, and the hook strand labels are unmasked by release of the link to their respective anchor strands. The two labels may be the same or different.

In another embodiment, the capture AB and the detection AB are both linked to the anchor strand, allowing concomitant control over capture and detection AB densities whilst maintaining colocalization at the nano-scale, potentially allowing more accurate control of assay performance (such as shown in FIGS. 5F-G, and some embodiments in FIG. 21). In such embodiments, the capture and detection ABs are colocalized and their relative density is the same, and can be modulated at the same time. One potential advantage of this embodiment is a homogeneous average-distance between capture and detection ABs for all pairs on a support. A second potential advantage of this embodiment is that the architecture of the capture and detection ABs may be precisely controlled. For example, by decreasing the length of the single-stranded portion of the anchor strand or the hook strand, the stringency of binding may be controlled, providing a deterministic means to control thermodynamics of the assay system. It will be appreciated by those skilled in the art that increasing the stringency of binding can lead to a decrease in effective affinity. In some embodiments, such tuning of the effective affinity can be used, among other applications, to control and extend the dynamic range of the assay.

In some such embodiments where the effective affinity can be tuned by changing the length of the hook strand or the anchor strand (i.e., the linker length), or by tuning the surface densities of capture and detection ABs, multiplexed arrays (such as multiplexed microparticles) can be fabricated that are designed with different effective affinities. This can be useful to extend the dynamic range of a particular assay for a particular analyte. For example, those skilled in the art will appreciate that some proteins are present in blood in concentrations ranging >5 orders of magnitude; for such targets, several assays can be designed, with different barcodes, to be able to quantify such proteins over a larger dynamic range.

In an embodiment, a capture AB is conjugated to a capture oligonucleotide which hybridizes to one sequence domain of the support-linked anchor strand. Another sequence domain of the anchor strand may be hybridized to the hook strand which is linked to the detection AB. All the aforementioned strategies for signal transduction and generation can also be utilized in this embodiment.

In an embodiment, two or more sets of distinguishable (i.e., multiplexed) complexes detecting the same target can be designed to increase the dynamic range of a multiplexed assay, wherein the lengths of the hook strand oligos for the two or more sets, and hence the stringency of the binding, can be controlled. For example, two or more sets of microparticles with different barcodes but targeting the same analyte can be fabricated, wherein the first microparticle set includes a shorter hook strand oligo to reduce flexibility and increase stringency of binding, and wherein the second microparticle set includes a longer hook strand oligo to increase flexibility and reduce stringency of binding, and so on. In this way, the first microparticle set can be designed to quantitate the analyte when it is present at higher concentrations.

Those skilled in the art will recognize that another challenge of multiplexed assays is interference and matrix effects, which can be difficult to control at the analyte-level. One of the advantages of methods and systems provided herein, in some embodiments, is the ability to contact the same biological sample with multitudes of assay configurations within the same assay volume. This flexibility may provide the ability to individually control for matrix effects on specific ABs and assay reagents. For example, certain samples could contain endogenous antibodies and other molecules which could positively or negatively impact the intensity of the assay signal for specific analytes.

In another embodiment, there are provided distinct supports or biomolecule complexes, with every analyte-specific support lacking either one of the capture or detection ABs and acting as an analyte-specific internal standard that controls for matrix effects and other potential modes of failures of the assay. The assay signal of the fully-formed biomolecule complex on the support can then be compared to these single-AB controls. These internal controls can be used as flags for potential false positives.

Figure 13:
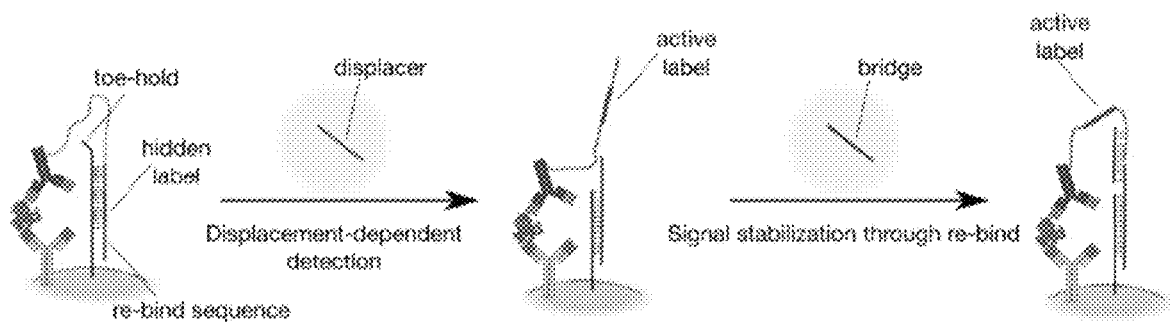
FIG. 13 shows a schematic diagram illustrating an embodiment of CLA used to stabilize signal after displacement, and before detection, using a re-bind mechanism. In this embodiment, the hook strand oligo includes a label sequence, and a re-bind sequence; after displacement with a displacer agent oligo that binds to the anchor strand and optional washing, a bridge strand binds to both the re-bind sequence and the anchor strand, thereby reconnecting the hook strand indirectly to the anchor strand. In this way the hook strand is re-attached to the support, along with the active/detectable label and the detection AB to which it is linked.

Those skilled in the art will recognize that another challenge of assays, particularly when using binders with non-zero or fast off-rate (k-off), is the unbinding of analytes, and hence drop in the assay signal, that can occur in the time between the washing of the biological sample to the read-out of the assay signal. This unbinding is especially problematic for low concentration analytes, and read-out methods that cannot measure the different assays in multiplex (e.g. cytometry). This problem may also be present in the CLA sensor procedure, whereby post-release (e.g., post-displacement), unbinding of the analyte to either the capture AB or the detection AB may result in signal loss. In yet another embodiment, therefore, the CLA methods and systems provided herein can be modified to mitigate this problem of unbinding and time-dependent signal by transducing the assay signal from a reversible reaction (e.g., an AB-analyte) into a stable oligo hybrid to stop further unbinding and is linked to the support enabling storage and read-out at a later time (such as shown in FIG. 13). A potential advantage of this embodiment is minimizing signal loss after assay completion which could help to increase sensitivity. Another potential advantage of this embodiment is the normalization of signal drop across different assays and samples that may be read out over a non-negligible amount of time, enabling better signal reproducibility and improved precision. In some such embodiments, an assay may be conducted similarly to previous embodiments, wherein the assay label is a unique DNA sequence, wherein following washing of released detection AB, a replacement agent can be introduced to re-link the hook strand back onto the anchor strand, thereby conserving the signal on the support. As those skilled in the art can appreciate, another potential advantage for this embodiment is reproducibility of the signal intensity, and, particularly, removing any dependence of the assay signal on time-to-measure and temperature.

In some such embodiments, there is provided a displacer agent which is an oligo that displaces the anchor strand-hook strand hybrid by binding to the anchor strand oligo via a toe-hold displacement reaction, followed by washing of released and unbound hook strand oligo-detection AB complexes, followed by addition of a replacement oligo that enables re-binding of the hook strand oligo to the anchor strand oligo by hybridizing to both oligos.

Figure 9:
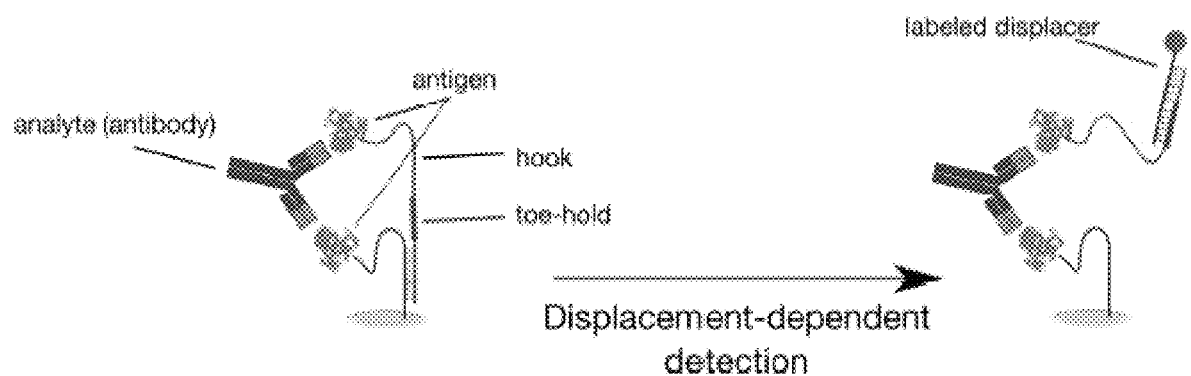
FIG. 9 shows a schematic diagram illustrating an embodiment of CLA with displacement-dependent detection for sandwich antibody detection. Identical antigens (e.g., peptides) are used as both capture and detection ABs, wherein one of the antigens is attached to a hook strand releasably attached to the anchor strand. Toe-hold mediated displacement using a labeled displacer agent (an oligo in this embodiment) performs the dual-function of displacing and labeling the hook strand. Fractions of labeled and released hook strands (shown) remain attached to the support only in the presence of the target antibody.

Several applications will benefit significantly from the methods and systems provided herein, which serve in some embodiments to address several sources of background noise and false-positives in multiplexed sandwich assays. In particular, in some embodiments multiplexing of protein analyses will be significantly enabled by the methods and systems provided herein. For example, profiling of proteins such as cytokines and other soluble factors has been limited in conventional multiplexing due to reagent-cross reactivity. In some embodiments, methods and systems provided herein can significantly improve multiplexed serological analyses. For example, multiplexed autoantibody assays that are used to detect many specific autoantibodies have been severely hindered by specificity. Autoantibodies are typically captured by specific recombinant or native antigens on a solid-support, and are then detected by a species-specific detection antibody (e.g., anti-human Fc IgG). As a result, any non-specific binding of autoantibodies present in sera will be detected and often leads to a false-positive, making this type of assay a single-binder assay (in other words, limited to single-plex form). In contrast, methods and systems provided herein can be utilized to perform a dual-binder assay; that is, one where the analyte (here an autoantibody) is recognized and detected by two specific ABs (here, the specific antigen). In such embodiments, recombinant or native antigens can be divided into two fractions, representing capture AB and detection AB, that are conjugated to a capture strand and a hook strand, respectively, wherein the capture strand and the hook strand are both linked to the same anchor strand, wherein the anchor strand is attached to the support (as in FIG. 9). As discussed previously, the flexibility of the hook strand can enable simultaneous binding of the analyte (here an antibody) to the capture AB and the detection AB (here identical proteins that are conjugated to distinct strands with distinct functionalities). Following washing of unbound sample, signal transduction can proceed via labeled strand displacement, as described herein.

Figure 10:
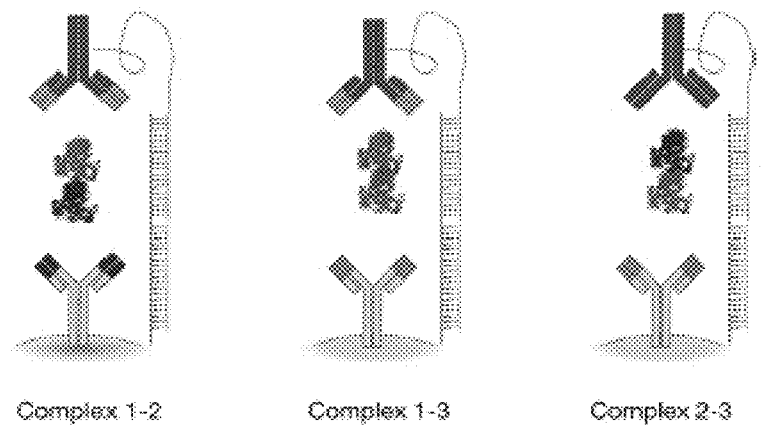
FIG. 10 shows a schematic diagram illustrating an embodiment of CLA used for detection of protein-protein interactions in multiplex, wherein arrays (planar or beads) are assembled with mismatched AB pairs, allowing detection of protein-protein interactions according to the AB pairs.

In some embodiments, methods and systems provided herein can address a major challenge in the multiplexed analyses of protein-protein interactions using ABs. For purposes thereof, AB pairs can be pre-assembled, each AB pair targeting one protein of interest, allowing for the CLA to detect interactions between the pair in question, as shown in FIG. 10. Because of the complete isolation of such multiplexed assays from another, cross-reactivity is reduced significantly, allowing combinatorial measurement of interactions across different protein-protein pairs. The modular approach of the fabrication method of the embodiments presented herein makes the implementation and fabrication of ABs pairs targeting different proteins relatively straightforward. For example, large batch fabrication of CLA on microparticles allows bulk functionalization of microparticles with capture ABs, followed by fractionation and addition of different detection ABs to every fraction.

In some embodiments, methods and systems provided herein can address another major challenge in the multiplexed analyses of post-translational modifications (PTM) using ABs. For example, accurate protein phosphorylation analysis can be used to reveal cellular signaling events not evident from protein expression levels. Current methods and workflows for quantifying the fraction of PTM of a specific protein are severely limited in multiplexing because PTM-specific ABs possess inadequate specificity for the protein itself (that is, a phosphor-specific AB is highly susceptible to the problem of reagent-driven cross-reactivity). As a result, conventional PTM panels are not multiplexed. The multiplexed CLA assay methods and systems provided herein can address this problem by confining the anti-PTM binder to an analyte-specific support (as in FIG. 11).

In some embodiments, a hook strand is a flexible and releasable linker and is an oligonucleotide, which allows for the formation of a capture AB-analyte-detection AB tertiary complex, such that upon release of one of the unbound hook strand oligos from the support, a signal is generated only in response to recognition of a sandwich capture AB-analyte-detection AB.

In some embodiments, there is provided a detection AB which is an antibody attached to a support, such as a microparticle, via a hook strand which is an oligonucleotide linked to the detection AB. The hook strand oligonucleotide is partially complementary to an anchor strand oligonucleotide attached to the support (e.g., microparticle) via a streptavidin/biotin interaction for example or a chemical bond, thus attaching the detection AB to the support. There is further provided a capture AB which is an antibody attached to the support and wherein the detection AB recognizes the same antigen but not the same epitope as the capture AB. In some embodiments, there is provided a displacer agent which is an oligonucleotide which contains a fluorescent label or a DNA barcode sequence and has a sequence complementary to the hook strand oligonucleotide, overlapping with the sequence of the anchor strand oligonucleotide so that the detection AB is released from the anchor strand oligo and thus may be released from the support in the absence of the target analyte. It should be understood that once the capture AB and the detection AB bind to the analyte, a tertiary capture AB-analyte-detection AB complex is formed on the support (e.g., on the microparticle). After formation of the tertiary complex, unbound detection AB is removed from the support by washing, while the tertiary complexes are retained on the support. The presence of the tertiary complexes on the support afterwards can be detected and/or quantified.

In some embodiments, methods and systems provided herein may be referred to as "colocalization-by-linkages assay on microparticles" or "CLAMP". CLAMP methods and systems described herein may be highly accessible and advantageous for users. For example, by providing microparticles that have pre-assembled AB pairs (pairs of capture and detection ABs), users can rapidly mix-and-match panels at will, perform multiplexed assays rapidly, and read-out the assay results using e.g. any multicolour flow cytometer. CLAMP assays provided herein can thus fit within existing experimental workflows in biology, and in some embodiments can be read out using any multicolor flow cytometer.

It will be appreciated that CLAMP embodiments are uniquely amenable for large, industrial-scale fabrication of multiplexed panels that avoid cross-reactivity. As opposed to planar arrays, CLAMPs can be fabricated separately in large batches, optionally stored, and then mixed prior to the assay.

This fabrication method allows CLAMPs to be manufactured independently without interaction between non-cognate ABs, and hence without cross-reactivity during the manufacturing step, a key advantage over other CLA embodiments.

In some embodiments, to fabricate multiplexed CLAMPs, AB pairs are attached on sets of microparticles, wherein each target-specific AB pair is attached on its respective set of microparticles in a separate vessel. The microparticles can be barcoded prior to the AB attachment, or can be barcoded during this process as well. This reaction can be performed in large batches, and the fabricated CLAMPs can be stored. To conduct an assay, fractions of beads for each barcode/target are mixed together before contacting with the biological sample. Microparticles can be barcoded using any means, for example spectrally, graphically, or chemically.

In some embodiments, where the support is a microparticle (MP), certain advantages may be obtained. For example, in some embodiments the ability to rapidly read out a large number of MPs by flow cytometry can afford increased precision and sample throughput In addition, MPs may be functionalized in large batches and then stored, used, and read-out while in solution, which can reduce lot-to-lot variability and enable quantitative analysis (Tighe, P. J., et al., Proteomics-Clinical Applications 9, 406-422, 2015; Jani, I. V., et al., The Lancet 2, 243-250, 2002; Krishhan, V. V., Khan, I. H. & Luciw, P. a. Multiplexed microbead immunoassays by flow cytometry for molecular profiling: Basic concepts; Tighe, P., et al., Utility, reliability and reproducibility of immunoassay multiplex kits. Methods (San Diego, Calif.) 1-7 2013; Fu, Q., et al., Clinical applications 4, 271-84, 2010).

Figure 2:
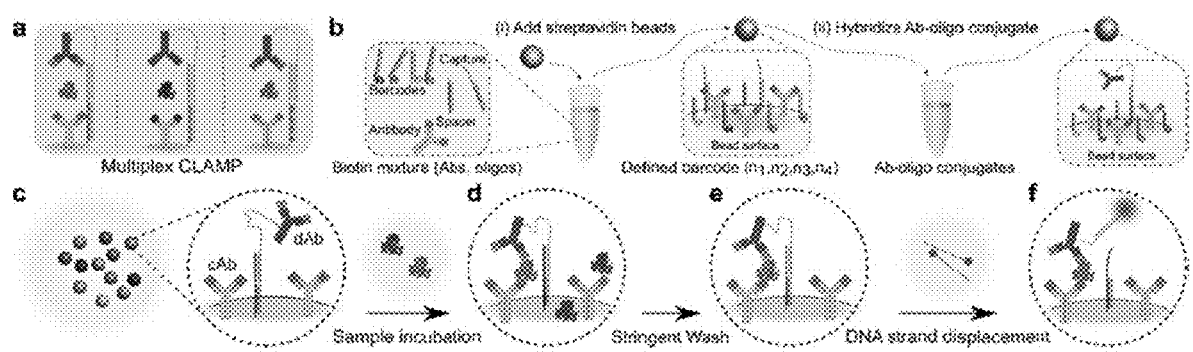
FIG. 2 is a schematic diagram that illustrates certain embodiments of the technology. (a) shows a CLAMP system in which cross-reactivity is prevented by colocalizing antibody pairs on individual beads using DNA linkages. In (b), each member of a CLAMP panel is made via one-pot fabrication of beads with a capture antibody (cAb) and ratios of fluorescent barcoding signals. In (c), bead sets, each with a cAb and a pre-hybridized detection antibody (dAb), are mixed to form a CLAMP panel. In (d), sample addition and target protein binding is shown. In (e), washing removes biomolecules bound non-specifically. In (f), sandwich complexes on each bead are labeled via a fluorescent DNA strand-displacement of the dAb.

In some embodiments, methods and systems provided herein can reduce or eliminate reagent cross-reactivity. As shown in FIG. 2a, which illustrates one embodiment of CLA, the pre-colocalization of two sets of antibodies on a surface using DNA oligonucleotides as flexible and addressable linkers, can eliminate interaction between non-cognate antibodies. Further, upon release of one of the flexible linkers from the surface, a signal is generated only in response to a sandwich antibody-antigen-antibody recognition.

FIGS. 2B-2F show the nanoscale architecture and operating principle of CLAMP, in accordance with one embodiment. CLAMP populations were created through a one-pot functionalization of microparticles with defined ratios of fluorescent oligonucleotides and antibodies (FIG. 2B), followed by hybridization of hook oligo-detection Ab (dAB) complexes to complete the construction of the CLAMP (FIG. 2B). In an embodiment, stable biotin-streptavidin bonds are used for reagent linkages/attachments, with bead sets stored after fabrication. Next, monovalent antibody-oligo conjugates are assembled as pairs on the barcoded bead sets via hybridization (i.e., antibody pairs A1-A2 and B1-B2 are pre-assembled on beads A and B, respectively) (FIG. 2C), and bead sets are then pooled together. When a CLAMP panel is added to a sample, target proteins generate sandwich complexes, while non-specifically bound proteins do not form complete sandwiches (FIG. 2D). After incubation, stringent washing removes non-specifically bound proteins (FIG. 2E). Next, DNA strand displacement is used to simultaneously dehybridize and label one antibody of the sandwich on each bead population, which ensures that only sandwich binding events generate a signal (FIG. 2F). Finally, CLAMP panels are automatically read-out and bead sets decoded using any commonly available multicolor flow cytometer.

In some embodiments, CLAMP panels can have lower development costs than traditional immunoassays; not only is costly re-optimization of panels avoided as new target analytes are added, but CLAMP can also use significantly lower quantities of antibodies per assay.

In some embodiments, in addition to overcoming reagent cross-reactivity, the pair of surface-tethered antibodies in CLAMP can result in a binding avidity effect, giving CLAMP further advantages over conventional sandwich immunoassays. CLAMP can exhibit a higher affinity for targets, as the off-rate (koff) of targets from antibody sandwich complexes in CLAMP can be much lower than in assays using sequential antibody addition. In some embodiments, CLAMP assays can be stringently washed after incubation, reducing assay background and improving specificity. In addition, in some embodiments CLAMP may have a reduced liability for false positives: mis-binding events in CLAMP do not form complete sandwich complexes, and hence they do not lead to false positive signals.

EXAMPLES

The present invention will be more readily understood by referring to the following examples, which are provided to illustrate the invention and are not to be construed as limiting the scope thereof in any manner.

Unless defined otherwise or the context clearly dictates otherwise, all technical and scientific terms used herein have the same meaning as commonly understood by one of ordinary skill in the art to which this invention belongs. It should be understood that any methods and materials similar or equivalent to those described herein can be used in the practice or testing of the invention.

Example 1

One-Pot Bead Barcoding and CLAMP Manufacturing

In some embodiments, the multiplexed assay system was implemented on spectrally-encoded beads, wherein a one-pot bead barcoding strategy and automated decoding method can be used in methods and systems provided herein. Examples of such barcoding/decoding methods are described in U.S. patent application Ser. No. 16/153,071 and in Dagher, M. et al., Nature Nanotechnology, vol. 13, pp. 925-932, 2018, the contents of each of which are incorporated by reference herein in their entirety. Such methods use accurate models of fluorophore spectral overlap and multicolor Forster-resonance energy transfer (FRET). For example, such strategies may have a capacity for more than 580 barcodes using two lasers for barcoding and a third laser for assay readout (shown in FIG. 3A). Cytometers with infrared lasers can potentially expand the capacity to more than 5,000 barcodes.

The same manufacturing workflows were used to build a version of a colocalized antibody assay as described herein. Namely, in a first step, streptavidin beads were co-coupled with biotinylated capture antibodies and biotinylated anchor or capture oligos modified with different dyes to yield a distinguishable barcode. Each barcode, and target-specific antibody, were fabricated in separate tubes. In a second step, the detection antibodies (monoclonal) conjugated to a hook oligo were added to the corresponding functionalized beads from the first step. The hook strand oligo was complementary to the anchor strand oligo and hybridized to it, resulting in the assembly and colocalization of matched antibody pairs. The beads can be separately stored for use at a later time.

Figure 3:
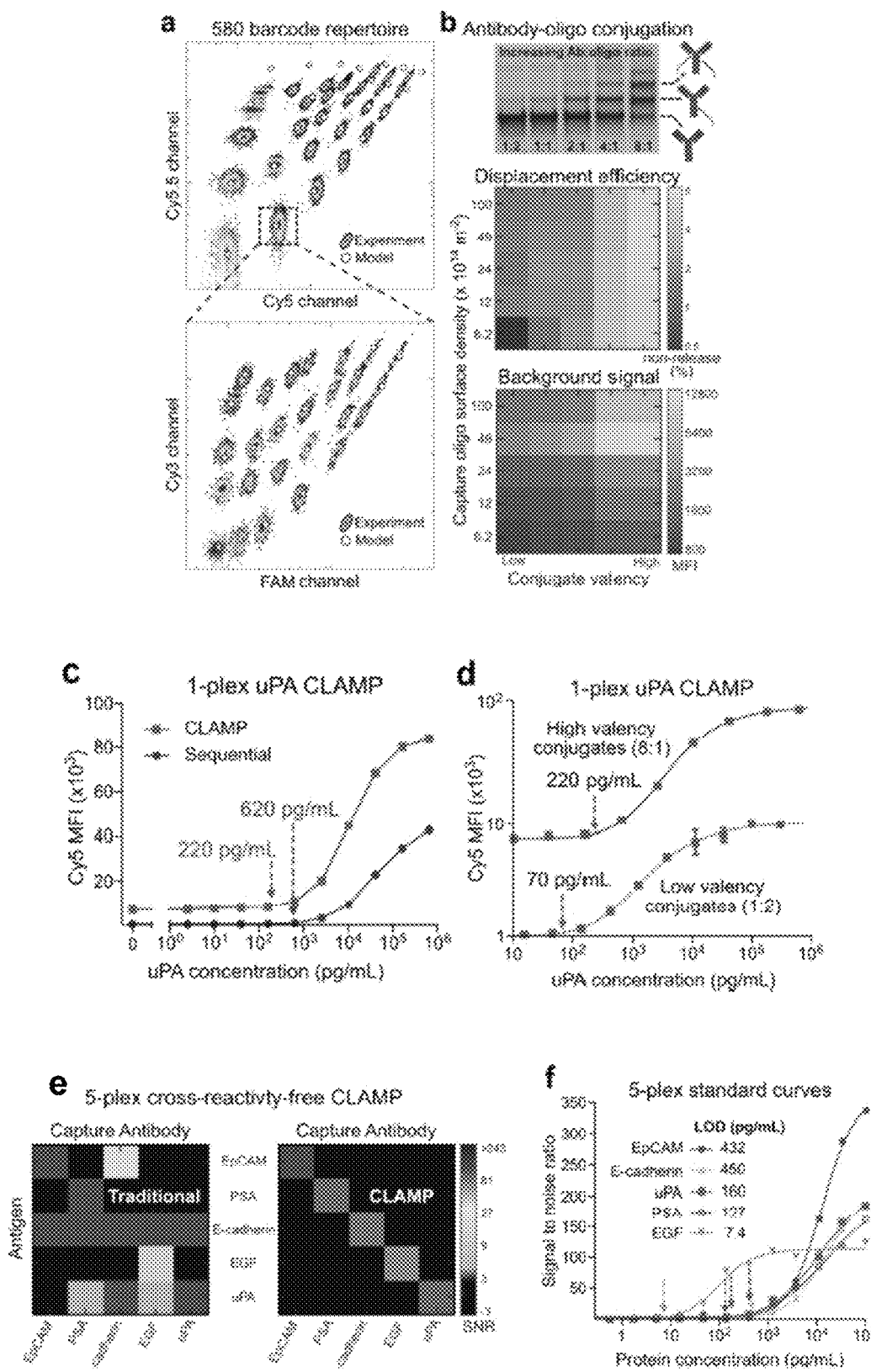
FIG. 3 shows a CLAMP assay in accordance with one embodiment of the technology, in which (a) shows an automated 4-color barcoding strategy, which permits >580 bead barcodes to be implemented on any multicolor cytometer; (b) shows low valency antibody-oligo conjugates dramatically improved strand displacement efficiency (>99%) and minimized assay background signals; (c) shows a 1-plex CLAMP for uPA led to increased sensitivity over a traditional (sequential) immunoassay on beads; (d) shows low valency conjugates improved CLAMP sensitivity further; (e) shows 5-plex CLAMP, assembled with antibody pairs that cross-react extensively in a traditional sandwich format, exhibited no cross-reactivity; and (f) shows individual standard curves for 5-plex CLAMP.

In some embodiments, a low oligo:antibody conjugation ratio or valency and/or two-step purification can be used to optimize (i.e., lower) background signal. For example, low valency antibody-oligo conjugates were shown to maximize CLAMP strand displacement efficiency and minimize background signal (FIG. 3B). After a first optimization round (varying ionic strength, washing and incubation times, nanoscale designs and reagent concentrations) the sensitivity of a 1-plex CLAMP for uPA was improved 3-fold over a traditional sandwich assay (FIG. 3C). Implementing monovalent, rather than high-valency, conjugates resulted in a further 3-fold improvement (FIG. 3D).

In one embodiment, a CLAMP system as described herein comprises the following components:
1) microparticles holding all the other components in place;
2) a type of capture antibodies (cAb) covalently coupled to the microparticle;
3) a type of detection antibodies (dAb) covalently linked to a hook oligonucleotide wherein the detection antibody recognizes the same antigen but not the same epitope as the cAb;
4) an anchor oligonucleotide (AO) linked to the microparticles via a streptavidin/biotin interaction, for example;
5) a stem oligonucleotide (SO) that is fully or partially complementary to the AO and thus renders it at least partially double-stranded;
6) a hook oligonucleotide (HO) covalently-linked to the cAb and partially complementary to the anchor oligonucleotide thus attaching the cAb to the microparticle; and
7) a displacement oligonucleotide (DO) having 2 functions:
   a) containing a fluorescent label and
   b) having a sequence complementary to the HO and overlapping with the sequence of the AO so that the dAb is released from the AO and thus released from the microparticle.

A 5-plex CLAMP using antibodies was assembled wherein the antibodies were highly cross-reactive in a conventional sandwich immunoassay, and confirmed that CLAMP completely avoided cross-reactivity (FIG. 3E). Standard curves for a 5-plex CLAMP are shown in FIG. 3F.

CLAMP was used to profile human serum. Conjugated antibodies and barcoded beads were independently stored for >1 month, and CLAMP yielded good spike-in recovery of PSA in serum (data not shown).

In an embodiment, the CLAMP system described herein is a 10-plex cytokine panel. Cytokines encompassed herein are for example, but not limited to IL1 to IL17, MCP1/3, TNF, EGF/R, and/or VEGF/R. In another embodiment, the CLAMP system encompassed herein is a 10-plex panel focused on breast cancer metastasis, targeting for example, but not limited to, HER2, CEA, p53 and/or CA15-3.

Example 2

CLAMP Assay Architecture

We prepared and tested a colocalization-by-linkage assay on microparticles (MPs) called "CLAMP", in accordance with one embodiment. CLAMP is a multiplexed assay designed to eliminate reagent-driven cross reactivity ("rCR") by colocalizing and confining each antibody pair onto a set of barcoded MPs, thereby avoiding interaction between non-cognate antibodies (FIG. 14C). Oligonucleotides(oligos) are used as programmable building blocks to implement the key molecular 'operations' of CLAMP, including (i) flexible linkage of detection antibodies (dAbs), (ii) on-demand release of dAbs, (iii) transduction of assay signals, as well as (iv) fluorescent barcoding of MPs. Here we detail the conceptual operation and experimental validation and optimization of a CLAMP assay and showcase its efficacy to eliminate rCR using reagents that otherwise strongly cross-react in a conventional MSA.

Figure 14:
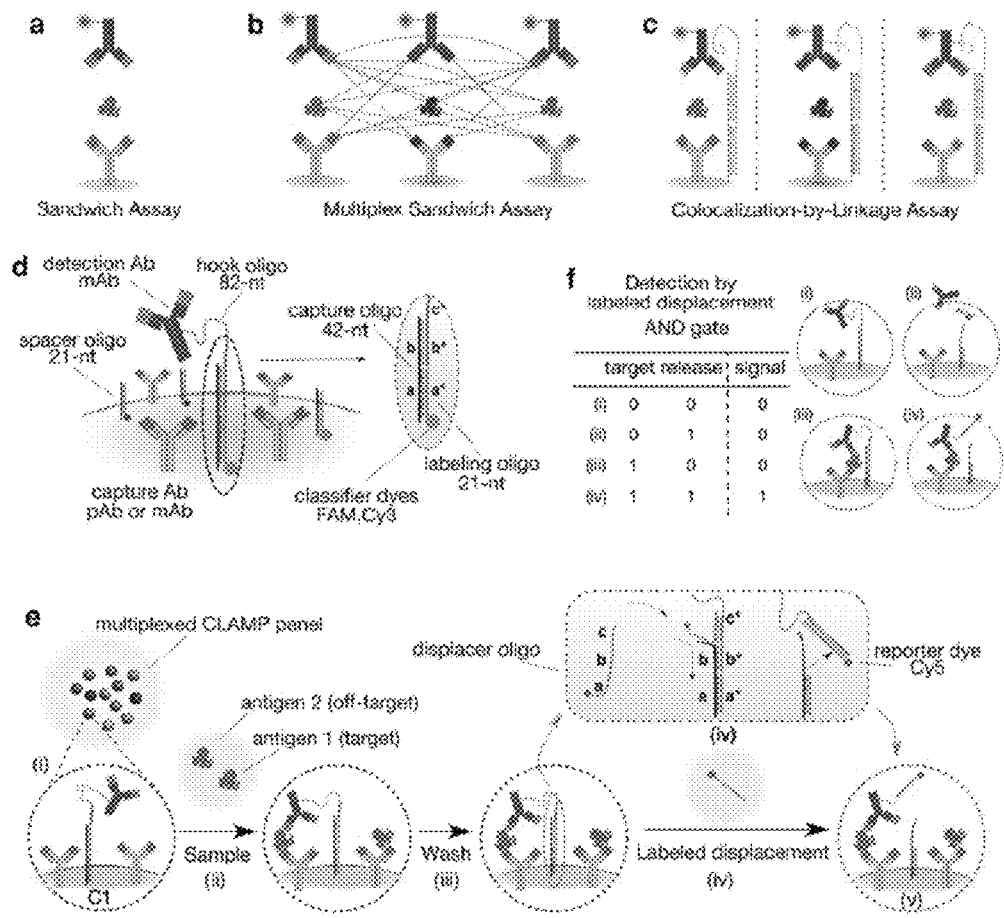
FIG. 14 shows a schematic illustration of single-plex and multiplex sandwich assays, and a CLA system on microparticles ("CLAMP"), in accordance with certain embodiments. (a) Single-plex sandwich immunoassay (also known as ELISA), comprising a pair of matched antibodies. (b) MSA with mixing of antibodies is exposed to a large number of interactions between non-matched antibodies and proteins, often resulting in rCR and false-positives. (c) CLAMP with pre-colocalization of antibody pairs using DNA linkage permitting sandwich binding while eliminating interaction between non-cognate antibodies. (d) The dAb is bound to a hook oligo (HO) that is tethered to the surface via partial hybridization with a capture oligo (CO) strand. A spacer oligo (SO) is used to control the density of the COs and dAb-HOs on the surface (see FIG. 19). (e) A multiplexed CLAMP assay is carried out by (i) mixing barcoded CLAMP microparticle against different targets, (ii) incubating the biological sample with microparticles generating sandwich binding in the presence of the target analyte only, (iii) washing, and (iv) displacing and labeling HOs using a fluorescently-labeled displacer oligo (DO) via toe-hold mediated displacement (inset), leading to (v) labeling of the sandwich complexes that remain on surface. (f) An AND (Boolean) logic gate representation of the detection by labeled-displacement step, where detection at the single-molecule level requires both the capture of target and successful HO release.

The architecture and operative principle of one embodiment, referred to herein as a CLAMP assay, are illustrated schematically in panels d and e of FIG. 14, respectively. To colocalize each pair of antibodies, an 82-nt hook strand oligonucleotide (referred to as hook oligo, or "HO") is covalently bound to a detection reagent which is an antibody, called a detection antibody or "dAb", and is partially hybridized via a 21-bp hybrid to a capture strand oligonucleiotide, called a capture oligo ("CO") bound to the surface of a capture reagent which is an antibody, called a capture antibody ("cAb")-coated microparticle ("MP"). Whereas the cAb is immobile on the surface, the dAb is flexible due to the HO's 61-nt single-stranded domain; this flexibility allows formation of a tertiary complex with the analyte (FIG. 14E). The confinement of antibody pairs precludes interaction between non-matched antibodies and restores the singleplex assay configuration on every MP, ensuring that single cross-reacting events (e.g. a target analyte reacting to a non-cognate cAb) do not lead to sandwich binding. A priori colocalization of antibodies allows for rapid dual-recognition of proteins but necessitates a concomitant method for signal transduction and generation. One approach would be to first break the HO-CO linkage. For example, via photo-induced or enzymatic cleavage, or toe-hold mediated displacement, then, after washing of the released dAb-HO complexes, label the dAbs remaining on the surface to signal sandwich formation. However, unbroken CO-HO linkages would result in labeling of the corresponding dAbs irrespective of the presence of the target analyte, which consequently increases the background signal. For example, 2% dAb coverage on a 3 µm MP corresponds to 1000-5000 dAbs that, if labeled, could result in a large increase in background signal and significantly impede sensitive detection.

Figure 7:
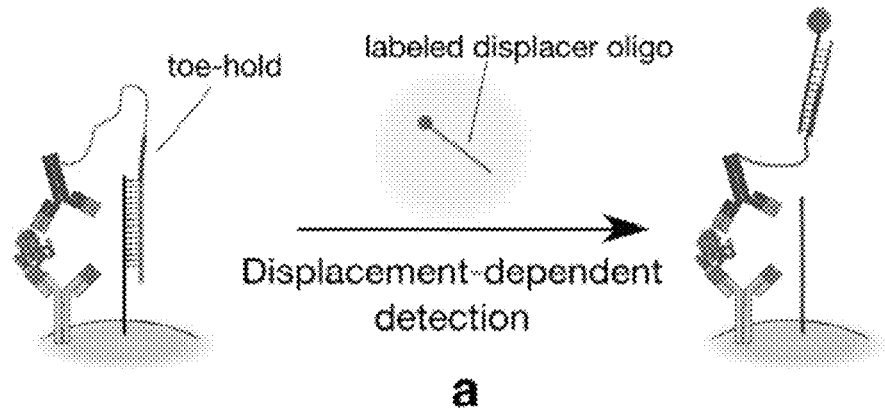
FIG. 7 shows a schematic diagram illustrating an embodiment of displacement-dependent detection. (a) A CLA embodiment is shown, wherein no label is present on the complex, and wherein the analyte is present and bound to both capture and detection ABs in a tertiary complex. A dye-labeled displacer agent, which is an oligo in this embodiment, binds preferentially to the hook strand oligo, simultaneously labeling the hook strand and displacing it from the anchor strand. (b) An AND (Boolean) logic gate representation of the displacement-dependent detection, where detection at the complex-level requires both the bivalent capture of target and successful hook-anchor displacement. Out of the different potential outcomes that consider the analyte presence and displacement success, the scenario shown in (a) is the only scenario that leads to a signal.
Figure 7:
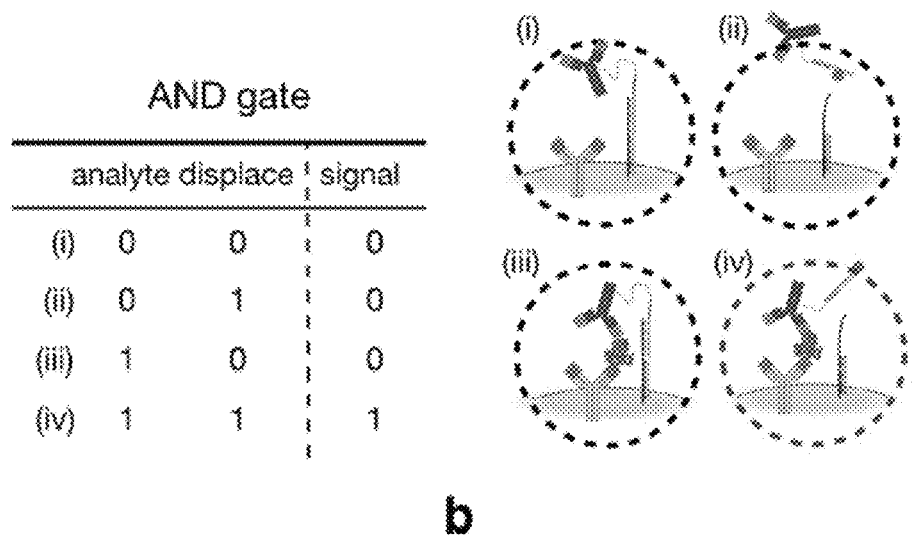
Figure 8:
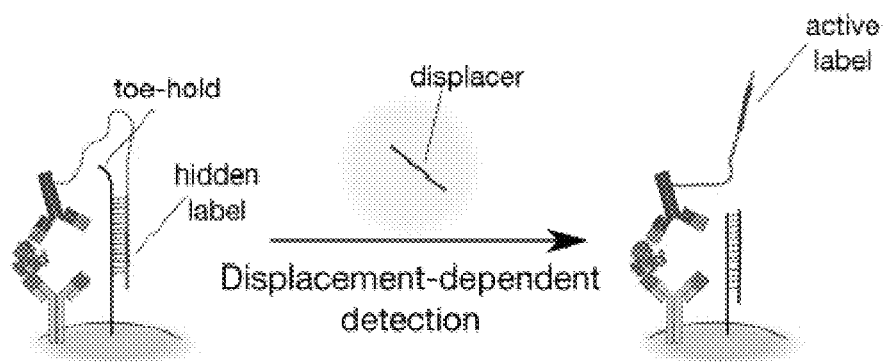
FIG. 8 shows a schematic diagram illustrating an embodiment of displacement-dependent detection wherein the label is a unique DNA sequence that is initially undetectable (i.e., unavailable for binding) because it is masked or hidden by hybridization to the anchor sequence. In the embodiment shown in this figure, the unlabeled displacer agent hybridizes to the anchor's toe-hold sequence to trigger displacement of the hook strand oligo, resulting in the label (unique DNA sequence) being available for subsequent detection, either via secondary hybridization or other DNA detection and/or amplification methods, such as PCR.
Figure 18:
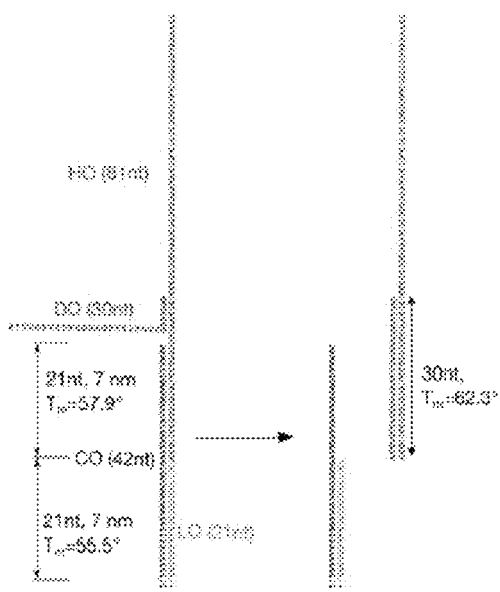
FIG. 18 shows sequences and melting temperatures of oligonucleotides used in CLAMP in accordance with one embodiment. The capture oligo (CO, 42 nt) is bound to the streptavidin surface via 5' biotin, and links both the 3' fluorescent labeling oligo (LO, 21 nt) and 5' antibody-conjugated hook oligo (HO, 81 nt) to the microparticle surface. A displacer oligo (DO $30nt$) initially binds to a 9 nt toehold on the hook oligo to displace the HO-CO hybrid.
Figure 19:
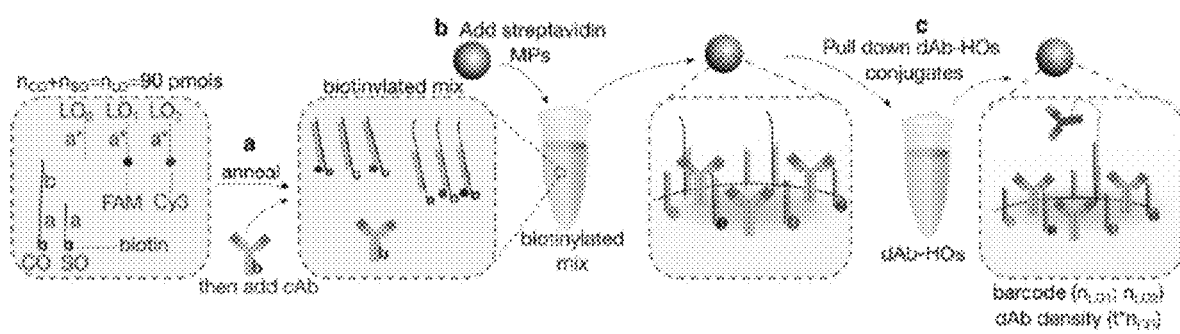
FIG. 19 shows a schematic illustration of synthesis of barcoded CLAMP microparticles, in accordance with one embodiment. Illustration describing the primary steps in the synthesis of the CLAMP microparticles. (a) Oligo constructs are pre-annealed and antibodies are added to form the biotinylated mixture of reagents. The mixture of biotinylated oligos includes precisely controlled proportion of CO/SO totalling 90 pmols and defining the CO (and later dAb-HO) surface density; the biotinylated oligos are annealed to a precisely controlled proportion of $LO_0/LO_1/LO_2$, totalling 90 pmols and defining the barcode. (b) Thereafter, streptavidin MPs are added to the biotinylated mix to proportionally and stochastically label them with reagents on the surface of the microparticles, wherein the relative densities of the oligo components (e.g. $LO_1/LO_2$) is conserved on the surface. (c) The dAb-HOs are finally pulled down on the surface to complete the synthesis of CLAMPs. The dAb density on the surface is proportional to the CO density, and hence, nco.
Figure 20:
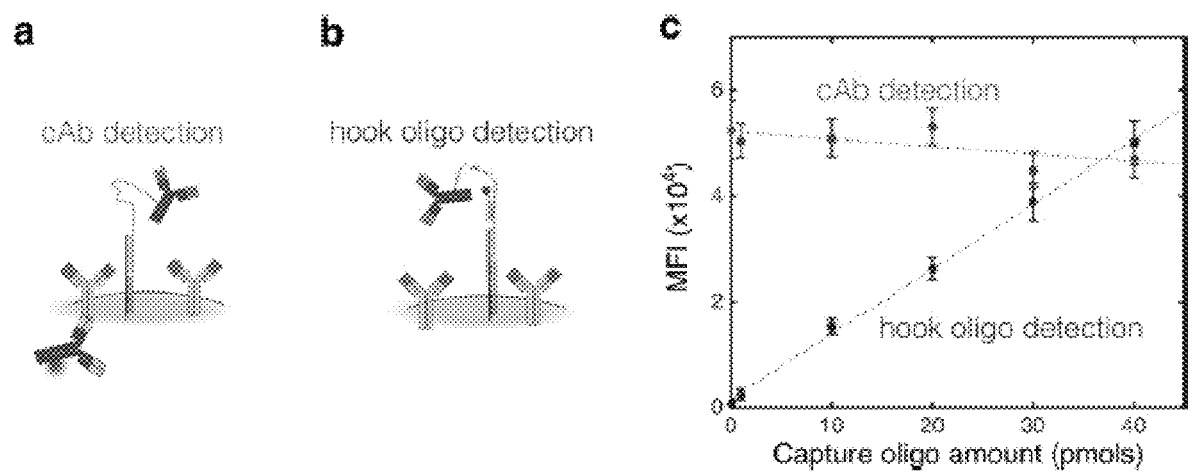
FIG. 20 shows a schematic illustration showing fine-tuning and accurate control of surface densities. (a) cAb detection using anti-goat antibody labeled with AF-647. (b) HO detection using a complementary, but non-displacing, oligo labeled with Cy5. Fluorescent intensities of CLAMP microparticles with varying CO reaction amounts, labeled using AF647 x-goat secondary antibody (red) and cy5-labeled oligos targeting the HOs (non-displacing, blue dots). (c) cAb and HO detection (in red and blue, respectively) for CLAMP prepared with increasing amounts of starting CO and decreasing SO such that nco+nso=90 pmols. Linear fits to the data are shown in dashed lines, and the error bars plot the standard deviation of the MP fluorescence.

To mitigate this effect in CLAMP assays, we designed a detection scheme to exclusively label 'successfully' released conjugates through the use of a fluorescently-labeled displacer oligo (DO) that binds to a toe-hold domain on HO, displacing and labeling it simultaneously (FIG. 14E, FIG. 7). Importantly, this 'detection-by-displacement' operates as an AND logical gate, requiring both protein dual-capture and dAb release for a detectable signal (FIG. 14F). In this embodiment, CLAMP reagents are assembled on magnetic MPs in two steps, benefitting from the affinity of biotin-streptavidin bond and Watson-Crick base pairing (FIG. 18). In a first step, a mixture of biotinylated oligos and antibodies are co-immobilized to the surface of streptavidin-coated MPs. The one-pot nature of the labeling affords accurate control over the CO surface density (FIG. 19), and simultaneously allows MP-encoding via one-pot labeling with multicolour classifier dyes, as described elsewhere (Dagher, M., et al., Nature Nanotechnology, vol. 13, pp. 925-932, 2018). In a second step, dAb-HO complexes are pulled-down via HO-CO hybridization to complete the assembly of CLAMPs.

Example 3

CLAMP Assay Optimization

We first optimized the efficiency of the toe-hold mediated displacement reaction by displacing unconjugated, Cy5-labeled HOs (FIG. 15). HOs were pulled down on MPs with different CO densities, then released using unlabeled DOs. Increased ionic strengths in the displacement buffer (MNaCl>500 mM) were helpful for screening the negatively charged oligos and improved the efficacy of DO hybridization to, and release of, the HOs. 98% displacement was reached over a wide range of CO densities with increased ionic strengths and DO concentrations (MNaCl~500 mM and MDO=1 µM, respectively).

Next, we studied the impact of antibody-oligonucleotide conjugates on assay background by measuring the residual signal on the MPs following a labeled-displacement step in buffer (see Methods below). We first conjugated HOs to immunoglobulin-G (IgGs) using a commercial kit (Solulink) leading to approx. 90% antibody conjugation yield and an average of 2 HOs per IgG (i.e., $\lambda$~2). Using these conjugates, the assay background was an order of magnitude greater than the assay background of unconjugated HOs (FIG. 16A). The increase in background signal was due to multivalent HO conjugates, which can result in unreleased dAb-HOs complexes (due to an unbroken HO-CO linkage) that are labeled by hybridization of a DO to at least one of the other HO strands, thereby generating a fluorescent signal in the absence of a sandwich binding with a protein (FIG. 16B). An effective way to minimize multivalent dAb-HO conjugates is to reduce the average conjugation valency; for example, by aiming for $\lambda$ of 0.1, Poisson statistics indicates that <5% dAb would be bound to multiple HOs. The trade-off of such a low conjugation valency is a decreased antibody conjugation yield (10%), which leaves 90% of antibodies unreacted. To avoid wasting unreacted antibodies, we developed a conjugation and purification workflow that maintains the native state of unconjugated antibodies and allows their recycling. The relative concentration of dAb and HO were adjusted and was modulated from 1.25 to 0.1 (FIG. 16C). The dAb-HO conjugates of varying valency were pulled down on MPs with varying CO densities. As expected, lower valency significantly decreased residual assay background, matching the background signal exhibited by unconjugated HOs for $0.1<\lambda<0.2$ (FIG. 16D), leading to low valency conjugates with fewer than 8% of multivalent conjugates. Consistent with a multivalent scenario, increasing CO density amplified the high background signals for higher valency dAb-HOs.

To optimize assay performance, we modulated the dAb-HO density. In CLAMP, adequate local dAb concentrations are key for sensitive and high capacity sandwich binding which, for a set HO length, is chiefly dependent on the surface densities of dAb-HOs and, through hybridization capture, COs. CLAMPs against urokinase plasminogen activator (anti-uPA CLAMP) with varying CO densities were prepared using low valency dAb-HO conjugates with fewer than 8% multivalent conjugates (FIG. 16D; see Methods below). anti-uPA CLAMPs were incubated with a serial dilution of recombinant uPA antigen, followed by washing and detection by labeled-displacement. As expected, increasing CO densities modulated the signal-to-noise ratio (SNR) of the assay, revealing that a density greater than $10^{14}$ $m^{-2}$ is necessary for adequate SNRs (FIG. 16E). Densities greater than $10^{14}$ $m^{-2}$, on the other hand, provided little improvement in SNR as they also resulted in increased background signal. Lastly, to assess the importance of conjugate valency on assay performance, we compared anti-uPA of high valency ($\lambda$~2, Solulink) against low valency conjugates ($\lambda$~0.1, FIG. 16F). The lower valency conjugates resulted in significantly lower background signals (10-folds) and, correspondingly, a 3-fold improvement in detection limits (FIG. 16F). On the other hand, low valency conjugates exhibited a decreased dynamic range of the fluorescence as sandwich-bound dAb-HO complexes are predominantly labeled with a single dye. Taken together, these results highlight the importance of conjugation valency on background signals and assay performance in general.

Example 4

Multiplexed CLAMP Assay

Figure 17:
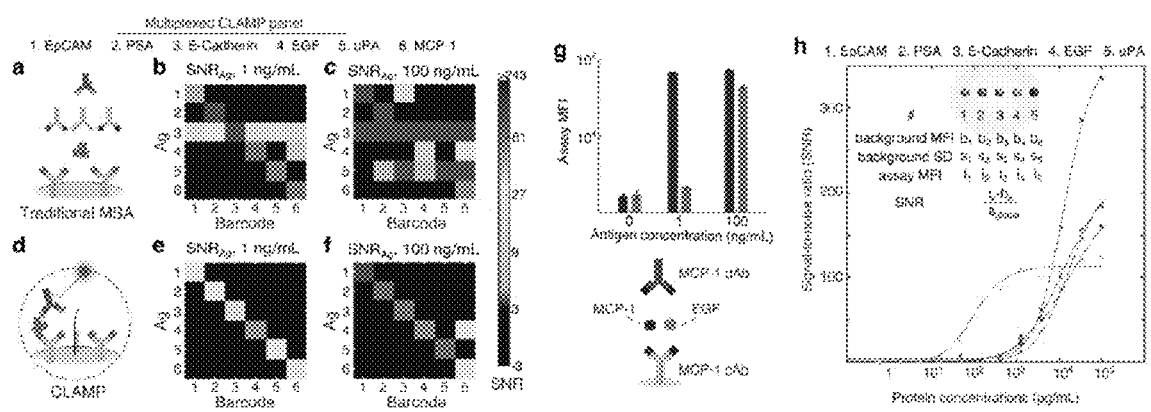
FIG. 17 shows elimination of cross-reactivity (CR) in CLAMP. Schematic representation of the CR screening performed for (a) conventional MSAs and (d) CLAMP assays, wherein the barcoded microparticles are mixed and incubated with one target at a time to reveal CR in a multiplexed format. SNRs quantifying specific (diagonal) and non-specific (off diagonal) assay signals for conventional MSAs (b, c) and CLAMP (e, f) in response to the addition of individual antigens at (b, e) 1ng/mL and (c, f) 100 ng/mL. (g) Assay MFI of a MCP-1 single-plex sandwich assay with MCP-1 (blue) and EGF (red) spike-ins at the specified concentrations (x-axis). (h) SNR signals of a 5-plex CLAMP dilution series. (inset) SNRs are calculated using barcode-specific backgrounds and global standard-deviations.

To test CLAMP's efficacy in eliminating reagent-driven cross reactivity ("rCR"), we screened the assay specificity of a multiplexed CLAMP in accordance with one embodiment. In addition, to challenge the CLAMP assay we selected antibody pairs that have been shown to exhibit different types of rCR when used together in a conventional multiplexed sandwich assay ("MSA"). To this end, antibody pairs against six targets (EpCAM, PSA, E-Cadherin, EGF, uPA and MCP) were shortlisted from a 35-protein panel that we previously characterized for specific and non-specific binding in a conventional MSA (Dagher, M. et al., Nature Nanotechnology, vol. 13, pp. 925-932, 2018). For conventional MSAs, the specificity screen consisted of incubating each individual antigen with a pool of cAb-coated barcoded MPs, followed by addition of mixed dAb cocktail and secondary-antibody ("sAb") for detection and labeling, respectively (FIG. 17A). Measuring the fluorescence across the different barcodes in response to an antigen concentration of 1 and 100 ng/mL (FIG. 17B-C) uncovered two types of non-specific binding that generated false-positives, namely indiscriminate sticking of antigens (observed for E-Cadherin and uPA) and cross-reactivity between antigens and antibodies. On the other hand, the specificity screen for CLAMP assays was performed by incubating a single antigen at-a-time with multiplexed CLAMPs and running the detection by labeled-displacement (FIG. 17d-f; see Methods below). All but one of the non-specific signals detected in conventional MSAs were completely eliminated using CLAMP assays. For example, the pervasive, non-specific binding of E-Cadherin, which led to a signal on all off-target beads in conventional MSAs, was not detectable in CLAMP assays. In contrast, cross-reactivity was detectable between MCP-1 antibodies and EGF antigen at 100 ng/mL both in conventional MSA as well as CLAMP. To investigate the source of this false-positive signal, we performed single-plex assays using MCP-1 antibodies only, separately spiking MCP-1 or EGF at 1 or 100 ng/mL (FIG. 17G). The detection of EGF by MCP-1 antibodies in single-plex indicated a dCR. Indeed, this dCR cannot be mitigated by CLAMP nor ELISA, and is an of poor affinity binders. Overall, these results showcase the strength of CLAMP in eliminating rCR in a multiplexed assay, as well as identifying dCR in multiplexed, combinatorial fashion. Finally, dilution curves of the remaining 5 proteins were generated and their SNRs were plotted as shown in FIG. 17H.

In summary, we successfully demonstrated use of CLAMP, a homogeneous MSA that uses oligonucleotides to precolocalize antibody pairs on MPs. By confining each antibody pair to their respective MPs during sample incubation, CLAMP can be multiplexed while maintaining single-plex assay environments on each MP and, in doing so, eliminates reagent-driven CR. Notably, the pre-colocalization of antibodies in CLAMP represents a departure from conventional sandwich immunoassays, where matched antibodies are separate at the beginning of the assay. To detect correct sandwich binding, we have shown that a labeled displacer oligo can be used to simultaneously release and label dAb-oligo complexes. We studied and demonstrated the importance of using monovalent antibody-oligo conjugates to avoid labeling unreleased complexes and increasing background signals. We have experimentally validated the assay, both in single-plex and multiplex, and screened the specificity of the assay in multiplex using five antibody pairs pre-selected for CR, demonstrating that CLAMP eliminates all rCR experienced in a conventional MSA.

CLAMP can provide several distinct advantages over currently available MSAs. First, CLAMP can be easily deployable as it does not necessitate dedicated equipment for readout or introduce new workflows. Second, CLAMP can be a rapid assay as it can be completed in little over three hours. Finally, by eliminating the need to incubate detection antibodies in solution (which is typically done at high concentrations), CLAMP can provide significant reductions in reagent consumption. Owing to its highly scalable and highly efficient nature, CLAMP can be used to provide a truly-scalable multiplexed ELISA platform that meets the increasing demands in biomarker discovery and drug development.

Example 6

Low Antibody Concentration Minimizes Cross-Reactivity in a CLAMP Assay

Conventional multiplexed sandwich immunoassays are commonly conducted with a mixture of reagents in the solution phase. In particular, the detection antibodies (dAbs) against different targets are mixed and applied to the reaction together. The application of such dAb cocktail leads to spurious binding and generates false-positive signals from non-specific binding events (between a cAb or dAb and a non-targeted analyte) that are difficult to discriminate from the real target protein-binding signal. The risk of reagent-driven CR scales as $\sim 4N^2$ with the number of target analyte N.

Figure 16:
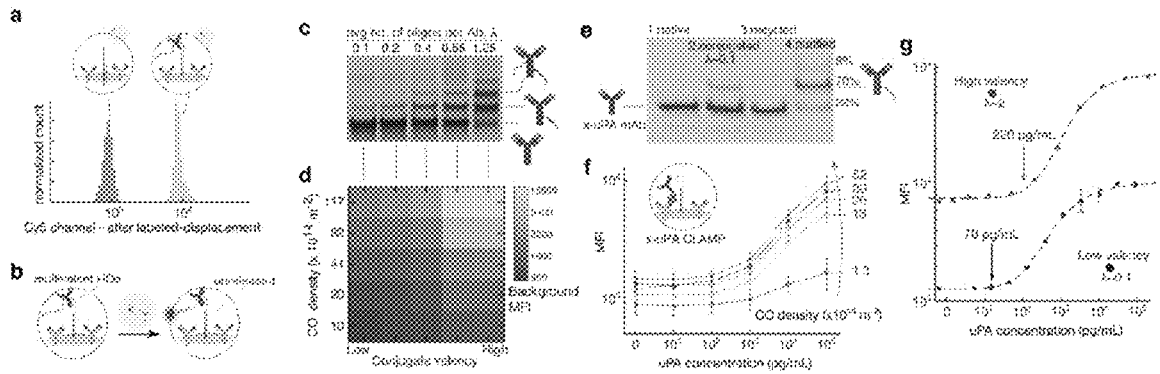
FIG. 16 shows CLAMP optimization by modulating conjugate valency and surface density. (a) Normalized histograms compare the CLAMP background signal (i.e. residual signal after incubation with Cy5-labeled DO) for microparticles without HOs (in blue) and with multivalent dAb-HOs conjugates (in yellow) (see FIG. 6). (b) Illustration depicting how multivalent dAb-HO conjugates may increase background signal by labeling unsuccessfully displaced dAb-HO complexes despite the absence of sandwich binding with the target analyte. (c) SDS-PAGE of mouse anti-goat IgGs conjugated with HOs with increasing valencies and stained by silver amplification. (d) Assay background MFI plotted with respect to increasing conjugate valency (columns) and increasing CO density (rows). (e) SDS-PAGE of low valency dAb-HO (mouse uPA mAbs) conjugates at different stages of the purification protocol where (1) native dAb, (2) conjugation product dAb-HO (non-purified), (3) recycled (non-conjugated) dAb, and (4) purified dAb-HO. (f) MFI assay values for x-uPA CLAMP assays against standard dilutions of uPA antigen and for varying CO densities. Error bars are standard-deviation of the microparticle signals in Cy5 channel. (g) MFI signals in x-uPA CLAMP assays using low (blue dots) and high (red dots) valency conjugates. Error bars are standard deviations of MFI signals across wells (n=3). The LODs shown on each curve are calculated as discussed in Methods below.

In contrast, in embodiments of CLAMP, reagent (e.g., antibody) pairs can be pre-assembled and colocalized on barcoded microparticles to avoid the reagents mixing. The detection antibodies (dAbs) will only be released in solution after the displacement reaction, as described herein. In some embodiments, to avoid re-binding on off-target beads after the displacement reaction, the dAbs released into solution should optimally remain at sufficiently low concentrations. FIG. 16 plots the dAb concentration profile with respect to the starting amount (y-axis) and volume of solution during the displacement step. The typical dAb concentration in a conventional ELISA is ~1 µg/mL (67nM), and with sufficiently-long incubation, binding can still occur when the dAbs are as low as 1 nM (such as in a Simoa assay by Quanterix).

Figure 22:
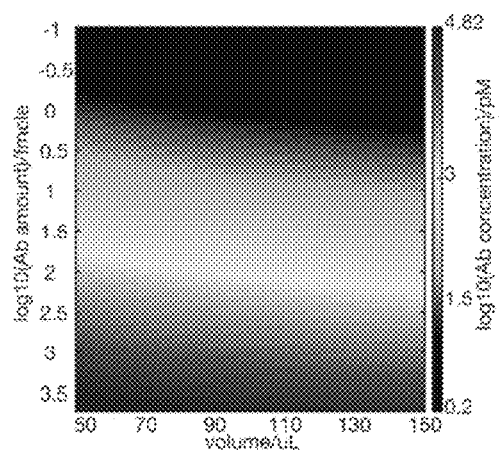
FIG. 22 shows a calculation of the displaced detection antibody concentration profile for a CLAMP assay in accordance with one embodiment, where the detection antibody concentration profile is plotted with respect to the starting amount (y-axis) and the volume of solution (x-axis) during the displacement step.

To ensure that off-binding is avoided after release, the amount of antibodies per target should ideally be kept <10 pM. In a volume of 100 uL, the amount of antibodies is <1 fmoles. In a CLAMP assay, in some embodiments, the amount of released Ab from 1000 microparticles was estimated to be 0.1-1 fmoles (FIG. 22). The numbers indicate that the dAb concentration released from the CLAMP system was significantly lower compared to other methods where free diffusion-based reagent mixing is required.

Example 7

Displacement-Dependent Signal Transduction Minimizes Background Signal in a CLAMP Assay In an embodiment of a CLAMP colocalized assay where both antibodies are pre-colocalized on the support, signal transduction could be performed by detecting all dABs remaining on the surface after release and washing. However, any non-released hook oligo-dAb complexes could result in an analyte-independent signal, significantly contributing to the background noise. Hence, it will be appreciated that to avoid increasing the background signal, in some embodiments a near-complete anchor-hook displacement and washing of hook oligo-dAB complexes are required.

In some embodiments, the problem of increased background signal due to inefficient release can be addressed through a displacement-dependent signal transduction mechanism. Such a mechanism would ensure that only displaced hook-anchor strands are detectable, and as such, non-displaced strands, which might occur due to inefficient displacement, do not yield a background signal. In such embodiments, signal transduction at the molecular level only occurs if both of the following conditions are satisfied: (i) formation of a tertiary complex, and (ii) displacement of the hook-anchor strands.

In some embodiments, therefore, the detection Ab and the hook strand are not labeled, and displacement occurs using a labeled (e.g., fluorescently-labeled) dispacer oligo. In this embodiment, the displacer oligo can bind to the hook strand preferentially which (i) releases it from the anchor strand and (ii) labels it. On the other hand, a non-displaced hook oligo is not labeled and does not contribute to the signal. This mechanism is equivalent to an AND gate where the signal (output) is dependent on both displacement (input 1) and analyte presence (input 2), as shown in FIG. 23.

To demonstrate the effectiveness of the displacement-dependent signal transduction, we performed calibration assays for IL-7, IFN-gamma, and MMP-9. In a first test, the displacer oligos were not labeled, and the mouse-dAbs were targeted using anti-mouse BV421 secondary antibody. The BV421-labelled secondary antibody was targeting at the dAb independent of whether it was released and hence the labelling occurred regardless of the displacement. In a second test, the displacement oligo was labeled using Cy5, which tested the displacement-dependent signal transduction. As shown in the logic gate representation chart (FIG. 23), the BV421 signal would be introduced in condition (i), (iii), (iv), but the Cy5 signal would only appear in condition (iv). Example calibration curves from the targets obtained by using the two labeling methods is shown in FIG. 24. The signal background from BV421 was significantly higher compared to the Cy5 signal, while the assay performance in terms of sensitivity and dynamic range were improved with the labeled-displacement (Cy5).

Example 8

Low Valency Antibody-Oligo Minimizes Background Signal in a CLAMP Assay

In some embodiments, the hook and anchor strands are DNA oligonucleotides. Antibody-DNA conjugation can be performed, for example, by targeting the lysine groups on an IgG molecule. Heterobifunctional linkers such as sulfosuccinimidyl 4-(N-maleimidomethyl) cyclohexane-1-carboxylate (sulfo-SMCC) can be used to therefore link a thiol-terminated DNA to an IgG molecule. This reaction, however, results a heterogenous conjugates, wherein the number of oligos per antibody is dependent on the stoichiometry of DNA:antibody during the reaction. Multivalent conjugates (more than one oligo per antibody) can reduce displacement efficiency and hence increase the background signal.

Figure 25:
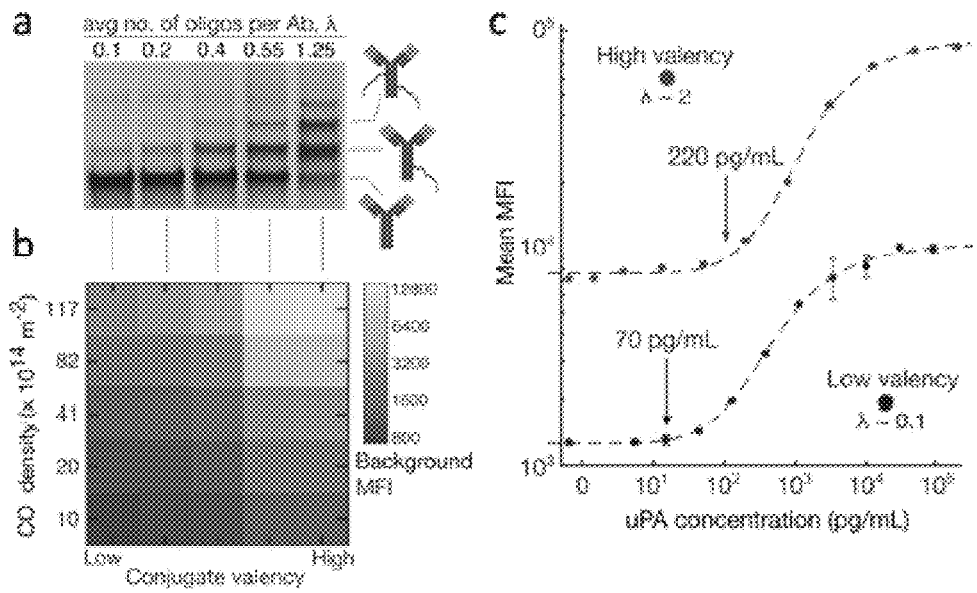
FIG. 25 shows CLAMP optimization by modulating conjugate valency. (a) SDS-PAGE of mouse anti-goat IgGs conjugated with HOs with increasing valencies and stained by silver amplification. (b) Assay background MFI plotted with respect to increasing conjugate valency (columns) and increasing CO density (rows). (c) MFI assay values for x-uPA CLAMP assays against standard dilutions of uPA antigen and for varying CO densities. Error bars are standard-deviation of the microparticle signals in Cy5 channel. (g) MFI signals in x-uPA CLAMP assays using low (blue dots) and high (red dots) valency conjugates. Error bars are standard deviations of MFI signals across wells (n=3). The LODs shown on each curve were calculated as discussed in Methods below.

As shown in FIG. 25A-B, we modulated the binding valency and determined it through SDS-page, and used the resulting conjugates to determine displacement efficiency. High valency conjugates resulted in increased assay background. As expected, a higher anchor strand oligo density resulted in further increase of the background signal. To determine the impact of high conjugate valency on the signal background, we performed a CLA assay using a displacement-dependent detection mechanism (FIG. 25C). High-valency ($\lambda$, avg, no of oligos per antibody ~2) and low-valency conjugates ($\lambda$~0.1) were used to generate calibration curves for uPA. Lower valencies resulted in lower background and improved sensitivity by 3-fold.

Example 9

Cross-Reactivity Characterization at 40-Plex

Figure 26:
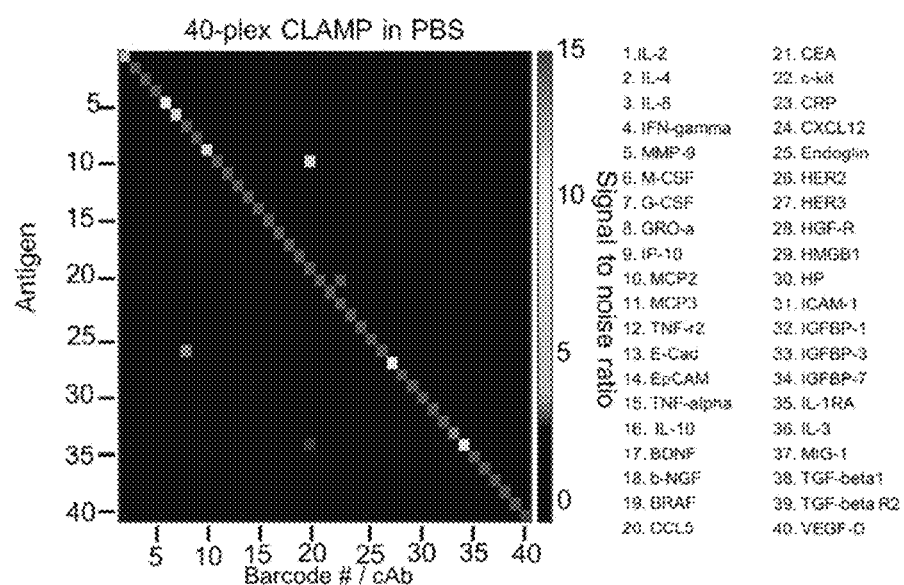
FIG. 26 shows a 40-plex specificity screening of a CLAMP assay, targeting 40 proteins (cytokines and others). Antigens (recombinant) were spiked one-by-one into buffer containing a mixture of multiplexed CLAMPs. Every well contained only one antigen. Detection, read-out, and plotting of the signal-to-noise ratio for every CLAMP for every well indicated minimal interaction of antigens with off-target CLAMPs, as shown by the minimal off-diagonal signals in the heatmap.

To assess cross-reactivity in multiplexed assays with higher multiplexing, a panel of 40 targets was tested, wherein mixtures of CLAMPS against 40 targets (as shown in FIG. 26) were mixed together and incubated in buffer spiked with one of the targets (a protein standard, typically recombinant) at high concentration (100 ng/mL) in each well. The signals seen on the diagonal indicate the specific interaction between the correct antigen and its barcoded microparticle pair. Only a few off-target signals were measureable; however, these were not due to reagent cross-reactivity. Instead, antigens were deemed to be cross-reacting with both antibodies, and hence would likely be noticeable for single-plex ELISA as well, as was demonstrated in FIG. 17.

Methods

Figure 11:
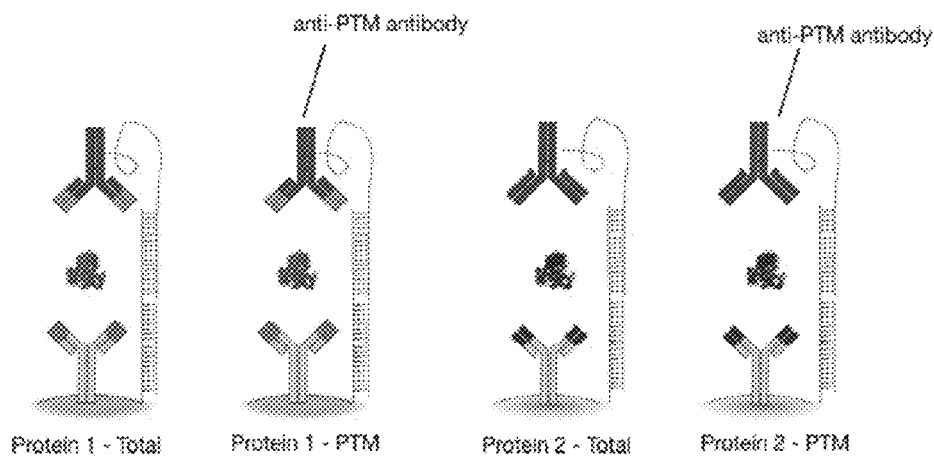
FIG. 11 shows a schematic diagram illustrating an embodiment of CLA used for detection of post-translational modifications (PTM) in multiplex, wherein arrays (planar or beads) are assembled with AB pairs targeting total and PTM-specific protein.
Figure 12:
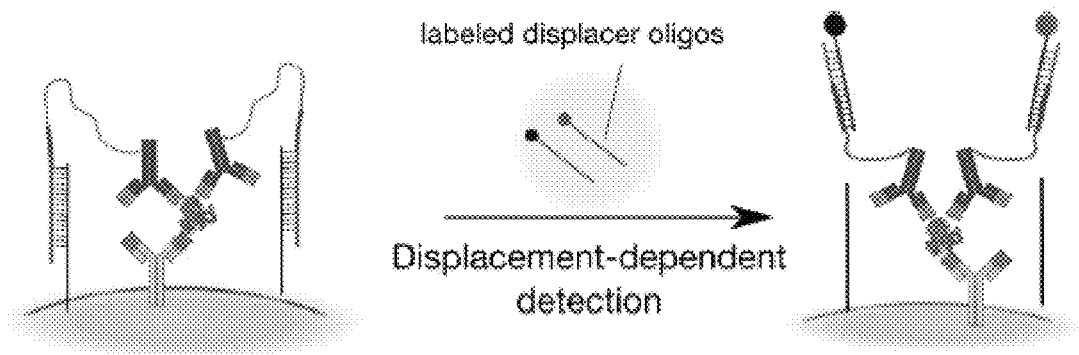
FIG. 12 shows a schematic diagram illustrating an embodiment of CLA where the capture reagent is an antibody attached directly to the support and there are two anchor strands. Each of the two anchor strands is linked by a DNA hybrid to a hook strand linked to a detection reagent (also an antibody). In the presence of analyte, a quaternary complex is formed. The hook strands are released, using labeled displacer agent oligos, from their respective anchor strands. The two labels may be the same or different.

Materials and Reagents. HPLC-purified oligonucleotides were purchased from IDT (Coralville, Iowa, USA); the sequences and modifications are shown in FIG. 11. cAbs, antigens, and dAbs were purchased from RnD Systems (Minneapolis, Minn., USA), and stored at −20° C. for up to 36 months. Streptavidin- and Protein-G magnetic MPs (M270) were purchased from Life Technologies (Carlsbad, Calif., USA).

Synthesis of CLAMPs. CLAMPs were assembled on streptavidin-coated magnetic MPs with a 2.7 µm diameter (M270-Streptavidin) in two steps. The first step consisted of the immobilization of a biotinylated mixture of antibodies and oligos to functionalize the MPs and simultaneously encode them as described in detail elsewhere (Dagher, M. et al., Nature Nanotechnology, vol. 13, pp. 925-932, 2018). Briefly, 90 pmols biotinylated oligos (COs, and SOs) and a total of 90 pmols of LOs (LO0-LO2) were mixed together in 25 µL of PBS+0.05% Tween20+300 mM NaCl (PBST0.05+ NaCl300). Whereas the proportions of each LO0:LO1:LO2 is designed to generate a unique ensemble fluorescence to define the barcode, the proportion of CO: SO allows tuning of the surface density of pulled dAb-HOs. The mixture is annealed by heating to 80 $C and cooling back to room temperature by removing the mixture from the heat source. Next, 5 µg biotinylated cAb in 17 µL of PBST0.05+NaCl300 were added to and mixed with the annealed oligonucleotide mixture. The biotinylated reagents are thereafter coimmobilized on the MPs in a single step by adding 3.25M MPs in 10 µL PBST0.05+NaCl300 and immediately mixing by pipetting. The mixture was incubated for 90 min with end-over-end mixing at room temperature, followed by 3x washing by magnetic aggregation in 150 µL PBST0.1. The barcoded and functionalized MPs were stored at 4 $C until needed. In a second step, 100,000 of the prepared MPs were mixed with the HO-containing solution (e.g. dAb-HOs) diluted in PBST0.05+NaCl300 for 30 minutes. After pull-down of HOs, the fully-assembled CLAMPs were washed 3x in PBST0.01, and were stored until the time of the assay for up to a week at 4° C.

Characterization of CLAMPs. To characterize CLAMPs, the immobilization of antibodies and oligos was confirmed by labeling using an anti-goat IgG conjugated with Alexa-Fluor 647 (AF647), or hybridization of a Cy5-labeled oligo (LO) targeting the HOs. The density of COs was estimated by fitting the ensemble fluorescence response of multicolour MPs using a multicolour fluorescence model, as described elsewhere (Dagher, M. et al., Nature Nanotechnology, vol. 13, pp. 925-932, 2018). To determine the expected assay background signal for a particular set of CLAMPs, the MPs were incubated with 1 µM Cy5-labeled DOs in PBST0.05+ NaCl300 for one hour, followed by 3x magnetic washing in PBST0.05, and the residual signal was determined by cytometry.

Antibody oligo conjugation, purification, and characterization. Anti-uPA monoclonal antibodies were conjugated to amine-modified HOs using a hydrazone chemistry (Solulink) followed by purification according to the manufacturer's protocol. Alternatively, monoclonal antibodies were conjugated to thiol-terminated HOs using a heterobifunctional amine/thiol-reactive crosslinker. 40 µL of 30 µM thiol-modified HOs were first reduced in 200 mM dithiothreitol (DTT) in PBST at 37° C. for one hour. The reduced oligos were (i) buffer exchanged into PBS pH 7.0 using a Zeba desalting spin-colum (7K MWCO, Thermo), (ii) activated for 10 min using 8 µL of 9 mM sulfosuccinimidyl 4-(N-maleimidomethyl)cyclohexane-1-carboxylate (sulfo-SMCC) dissolved in 80% PBS pH7.0 and 20% anhydrous dimethyl solfoxide, (iii) buffer exchanged again into PBS pH 7.0 to remove excess sulfo-SMCC, and (iv) a 1-10 µL fraction (depending on the desired) reacted with 10 µpL of 1 mg/mL antibodies. The reaction was left at room temperature for 1 hr and incubated overnight at 4 degrees C. thereafter. The conjugates were purified thereafter in two purification steps, an antibody and a DNA purification step, respectively.

Antibody oligo conjugation, purification, and characterization. Anti-uPA monoclonal anti bodies were conjugated to amine-modified HOs using a hydrazone chemistry (Solulink) followed by purification according to the manufacturer's protocol. Alternatively, monoclonal antibodies were conjugated to thiol-terminated HOs using a heterobifunctional amine/thiol-reactive crosslinker. 40 µL of 30 µM thiol-modified HOs are first reduced in 200 mM DTT in PBST at 37° C. for one hour. The reduced oligos were (i) buffer exchanged into PBS pH 7.0 using a Zeba desalting spin-colum (7K MWCO, Thermo), (ii) activated for 10 min using 8 µL of 9 mM sulfosuccinimidyl 4-(N-maleimidomethyl)cyclohexane-1-carboxylate (sulfo-SMCC) dissolved in 80% PBS pH7.0 and 20% anhydrous dimethyl solfoxide, (iii) buffer exchanged again into PBS pH 7.0 to remove excess sulfo-SMCC, and (iv) a 1-10 μL fraction (depending on the desired valency) reacted with 10 μL of 1 mg/mL antibodies. The reaction was left at room temperature for 1 hr and incubated overnight at 4° C. thereafter. The conjugates were purified in two purification steps.

Single-plex and multiplex CLAMP assay. Incubations were performed in a conical bottom 96-well plate at room temperature with horizontal shaking at 950 rpm. CLAMPS were mixed at roughly 80 MPs per barcode per μL and blocked with PBST0.05+NaCl150+0.5% BSA (PBST0.05+ NaCl150+BSA0.5) for 30 min. A 25 μL aliquot of the blocked, multiplexed CLAMP mixture was added into each well and incubated with 25 μL containing the specified antigen(s) at 2× the specified concentrations in PBST0.05+ NaCl150+BSA0.25, the incubation was performed for 3 hr at 950 rpm shaking. Magnetic aggregation and washing with 150 μL of PBST0.1 was repeated 4× in over a total of 30 min. Finally, detection-by-displacement is performed through the addition of 1 μM DO-Cy5 in PBST0.05+ NaCl300+BSA0.25 and incubation for 1 hr with shaking, followed by 3× washing in PBST0.1.

Conventional MSA. To screen the specificity and non-specific binding in conventional MSA format, MPs were barcoded and coupled with their respective biotinylated cAbs during synthesis as described above. MP mixtures were combined to a final concentration of 2,000 MPs per barcode per assay. Incubations were performed in a conical bottom 96-well plate at room temperature with horizontal shaking at 950 rpm. Prior to incubation with assay reagents, MPs were first blocked for one hour with 1% bovine serum albumin in 0.05% Tween-20 in PBS (PBST0.05). Incubation with antigens was conducted for 120 min at the specified concentrations. BMPs were incubated with the dAb cocktail for 60 min at 2 μg/mL, followed by incubation with sAbs for 45 mins at 4 μg/mL. SNRAg was calculated by subtracting the cAb-specific mean assay background (n=6) from the MFI signals and normalizing to the global standard-deviation (i.e. across all barcodes, n=210) of the assay background.

Read-out and data analysis. MPs were read out using the FACS CANTO II cytometer by BD with blue (488 nm), red (633 nm), and violet (405 nm) lasers. In blue-laser flow cell, 530/30 and 585/42 band-pass filters were used for FAM and Cy3, respectively. In the red-laser flow cell, 660/20 band-pass filter was used for Cy5/AF647, respectively. The MPs were decoded using an automated algorithm implemented on MATLAB (Dagher, M. et al., Nature Nanotechnology, vol. 13, pp. 925-932, 2018). All data analysis was performed in MATLAB. Single-beads were distinguished from bead aggregates and other particulates by using forward and side-scatter intensities and gating was automated.

While the present disclosure has been described in connection with specific embodiments thereof, it will be understood that it is capable of further modifications and this application is intended to cover any variations, uses, or adaptations, including such departures from the present disclosure as come within known or customary practice within the art to and as may be applied to the essential features hereinbefore set forth, and as follows in the scope of the appended claims.

The contents of all documents and references cited herein are hereby incorporated by reference in their entirety.

The invention claimed is:

1. A biomolecule complex for the detection or quantification of an analyte in a sample, comprising:
    (a) a support complex comprising:
        (i) a support;
        (ii) a capture reagent coupled with the support;
        (iii) an anchor oligonucleotide coupled with the support;
        (iv) a detection reagent coupled with a hook oligonucleotide, wherein the hook oligonucleotide is releasably coupled with the anchor oligonucleotide at a coupled region; and
    (b) a detectably-labeled displacer oligonucleotide configured to couple with the hook oligonucleotide at the coupled region and decouple the hook oligonucleotide from the anchor oligonucleotide;
wherein the capture reagent and the detection reagent are configured to simultaneously couple with the analyte.

2. The biomolecule complex of claim 1, wherein the analyte is coupled to the capture reagent and the detection reagent and the support complex further comprises the detectably-labeled displacer oligonucleotide coupled to the hook oligonucleotide.

3. The biomolecule complex of claim 1, further wherein the analyte is not coupled to one or both of the capture reagent and detection reagent and the support complex does not comprise the detectably-labeled displacer oligonucleotide coupled to the hook oligonucleotide.

4. The biomolecule complex of claim 1, wherein the anchor oligonucleotide comprises an anchor sequence and the hook oligonucleotide comprises a linker sequence complementary to the anchor sequence.

5. The biomolecule complex of claim 4, wherein the hook oligonucleotide comprises an additional sequence adjacent to the linker sequence and the detectably-labeled displacer oligonucleotide comprises a displacer sequence complementary to the additional sequence and at least a portion of the linker sequence.

6. The biomolecule complex of claim 5, wherein the displacer sequence is complementary to the linker sequence.

7. The biomolecule complex of claim 5, wherein the additional sequence comprises at least one nucleotide.

8. The biomolecule complex of claim 5, wherein the displacer sequence has a melting temperature greater than that of the anchor sequence.

9. The biomolecule complex of claim 1, wherein the sample is a biological sample.

10. The biomolecule complex of claim 9, wherein the sample is a bodily fluid, a whole blood sample, a cell supernatant, an extract, a cell extract, a cell lysate, a tissue lysate, a solution comprising nucleic acid molecules, or a solution comprising proteins.

11. The biomolecule complex of claim 1, wherein the capture reagent is selected from the group consisting of: an antibody or an antigen-binding fragment thereof, an aptamer, a modified aptamer, a somamer, an affimer, an antigen, a protein, a polypeptide, a multi-protein complex, an exosome, an oligonucleotide, a low molecular weight compound, and any combination thereof.

12. The biomolecule complex of claim 1, wherein the detection reagent is selected from the group consisting of: an antibody or an antigen-binding fragment thereof, an aptamer, a modified aptamer, a somamer, an affimer, an antigen, a protein, a polypeptide, a multi-protein complex, an exosome, an oligonucleotide, a low molecular weight compound, and any combination thereof.

13. The biomolecule complex of claim 1, wherein the capture reagent and the detection reagent are both antibodies or antigen-binding fragments thereof.

14. The biomolecule complex of claim 13, wherein the capture reagent and the detection reagent are a different antibody or antigen-binding fragment thereof and bind to a different epitope on the analyte.

15. The biomolecule complex of claim 1, wherein the detectably-labeled displacer oligonucleotide comprises a detectable label selected from the group consisting of a fluorescent polymer, a biotin molecule, a fluorophore, an enzyme, a nucleic acid enzyme, a riboswitch, an enzyme substrate, a specific nucleic acid sequence, and any combination thereof.

16. The biomolecule complex of claim 1, wherein the support is a microparticle, a nanoparticle, a well in a plate, an array, a microfluidic chip, a lateral flow strip, a slide, a porous polymer, or a hydrogel.

17. The biomolecule complex of claim 1, wherein the support complex comprises a plurality of the capture reagent, a plurality of the anchor oligonucleotide, and a plurality of the detection reagents coupled with the hook oligonucleotide.

18. The biomolecule complex of claim 1, wherein the detection reagent is coupled with a single hook oligonucleotide.

* * * * *